United States Patent
Manicke et al.

(10) Patent No.: US 12,205,808 B2
(45) Date of Patent: Jan. 21, 2025

(54) MASS SPECTROMETRY METHODS AND RELATED MATERIALS

(71) Applicant: THE TRUSTEES OF INDIANA UNIVERSITY, Bloomington, IN (US)

(72) Inventors: Nicholas Edward Manicke, Zionsville, IN (US); Brandon John Bills, San Jose, CA (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 377 days.

(21) Appl. No.: 17/777,191

(22) PCT Filed: Nov. 20, 2020

(86) PCT No.: PCT/US2020/061516
§ 371 (c)(1),
(2) Date: May 16, 2022

(87) PCT Pub. No.: WO2021/102268
PCT Pub. Date: May 27, 2021

(65) Prior Publication Data
US 2022/0406587 A1 Dec. 22, 2022

Related U.S. Application Data

(60) Provisional application No. 62/986,085, filed on Mar. 6, 2020, provisional application No. 62/938,777, filed on Nov. 21, 2019.

(51) Int. Cl.
*H01J 49/04* (2006.01)
*G01N 33/94* (2006.01)

(52) U.S. Cl.
CPC .......... *H01J 49/0409* (2013.01); *G01N 33/94* (2013.01); *G01N 2560/00* (2013.01)

(58) Field of Classification Search
CPC .. H01J 49/0409; G01N 33/94; G01N 2560/00
USPC ........................................ 250/281, 282, 288
See application file for complete search history.

(56) References Cited

U.S. PATENT DOCUMENTS

| | | | |
|---|---|---|---|
| 2012/0119079 A1 | 5/2012 | Ouyang et al. | |
| 2018/0033600 A1* | 2/2018 | Manicke | G01N 27/623 |
| 2021/0257204 A1* | 8/2021 | Pawliszyn | H01J 49/0409 |

OTHER PUBLICATIONS

PCT International Search Report and Written Opinion completed by the ISA/US on Mar. 9, 2021 and issued in connection with PCT/US2020/061516.

(Continued)

*Primary Examiner* — Nicole M Ippolito
(74) *Attorney, Agent, or Firm* — Barnes & Thornburg LLP

(57) ABSTRACT

Disclosed herein are mass spectrometry sample substrates. Also disclosed herein are mass spectrometry sample strips and cartridges that include a solid phase extraction (SPE) element. The mass spectrometry sample substrates, sample strips, and cartridges can be used in paper spray mass spectrometry to detect and quantify one or more analytes present in a biological sample. Also disclosed are methods for collecting and concentrating one or more analytes from a biological sample, as well as for storing a biological sample that includes one or more analytes. Methods for analyzing the one or more analytes from the biological sample are also provided.

17 Claims, 15 Drawing Sheets

(56) References Cited

OTHER PUBLICATIONS

Bills, "Studying and Modifying Paper to Lower Detection Limits for Paper Spray Mass Spectrometry." Diss. Purdue University Graduate School, Aug. 2019 (Aug. 2019), Figure 1.1, 4.3, p. 13, 90.

* cited by examiner

MASS SPECTROMETRY METHODS AND RELATED MATERIALS

CROSS-REFERENCE TO RELATED CASES

This application is a U.S. national counterpart application of international application serial No. PCT/US2020/061516 filed Nov. 20, 2020, which claims the benefit of U.S. Provisional Patent Application No. 62/938,777 filed Nov. 21, 2019 and to U.S. Provisional Patent Application No. 62/986,085 filed Mar. 6, 2020, the entire disclosures of which are hereby incorporated by reference in their entireties.

STATEMENT OF GOVERNMENT SUPPORT

This invention was made with government support under DA043037 awarded by the National Institutes of Health and 2016-DN-BX-0007 by the National Institute of Justice. The government has certain rights in the invention.

BACKGROUND

Cannabinoids

Cannabinoids, both natural and synthetic, have become increasingly important analytical targets. Marijuana and cannabidiol oil for recreational use in the United States has been decriminalized in an increasing number of states. Concurrently the use of synthetic cannabinoids (SCs) has increased. Synthetic cannabinoids are synthetically manufactured compounds that mimic the active ingredient of marijuana tetrahydrocannabinol (THC) in structure or function.

Historically, drug testing for marijuana use has been done in urine, and targets THC metabolites; commonly 11-Nor-9-carboxy-$\Delta^9$-tetrahydroannabinol (THC-COOH). Detection typically starts with an immunoassay for screening followed by gas chromatography-mass spectrometry (GC-MS) for confirmation. Liquid chromatography (LC)-MS is another potential technique, while alternate matrices for detection include blood, plasma, hair or oral fluid. Synthetic cannabinoids pose a problem for these traditional methods. Due to the large number of potential compounds and the wide variation in potency, immunoassays are not sensitive or selective enough. While chromatography methods combined with mass spectrometry are sensitive and selective, they often require extensive sample preparation, special training, and lengthy analysis times.

Ambient ionization techniques, such as desorption electrospray ionization (DESI), direct analysis in real time (DART), and paper spray mass spectrometry, directly analyze samples with minimal preparation. These methods have been investigated for their potential use in drug screening. Paper spray, in which biofluid samples are extracted and ionized directly from paper, is a potential option due to its low cost and short analysis time. Paper spray can detect certain analytes at sub-ng/mL concentrations. However, cannabinoids pose problems for paper spray for several reasons. For both natural and synthetic cannabinoids, the concentration in biofluids can be low and detection limits for paper spray are affected by matrix effects. This is especially problematic for THC and similar compounds, which are labile and degrade rapidly in dried sample spots through several pathways including photo and thermal degradation. Attempts to improve detection limits of paper spray have included adding a solid phase extraction component to a paper spray cartridge, performing a solvent extraction from the biofluid on top of hydrophobic paper and utilizing a membrane to filter out red blood cells from whole blood. These methods can help lower detection limits, but can also increase the cost and complexity of the analysis.

New Psychoactive Substances

New psychoactive substances (NPS), also called synthetic or designer drugs, are similar to historically more common drugs in structure or function and have been causing public health and safety concerns in the United States and around the world in recent years. These drugs have unique structures from their more well-known counterparts, making them more difficult to detect and regulate. Fentanyl and fentanyl analogs have been demonstrated to play a role in a drastic rise in the number of opioid-related overdoses in the United States. These analogues can have potencies that range over several orders of magnitude, making it is easy to overdose if the dosage isn't well controlled, or if heroin is cut with fentanyl. This has led to drug poisoning being the number one cause of injury deaths in the United States in recent years.

Another class of NPS, synthetic cannabinoids, present a different problem in that there are libraries of compounds available left over from pharmaceutical research into cannabinoids. These compounds are sprayed on dried plant material and marketed as incense "not for human consumption." The dosage of these compounds is often poorly controlled, the potency of each compound has not been studied, and there are unknown side effects. All of these factors result in patients ending up in the emergency room with an overdose on an unknown substance.

Traditionally, analysis of drugs of abuse involves an immunoassay screening step, followed by either gas or liquid chromatography paired with a detector. However, immunoassays are insufficient for screening in this new NPS crisis. The lethal concentrations of more potent NPSs are often below what immunoassays can detect in complex matrices like blood. Immunoassays are also not selective enough to tell different analogs apart from one another, nor are they able to easily implement multiplexing to determine whether multiple drugs are present. Chromatography paired with different detectors can have the required sensitivity and specificity, but is problematic for high throughput screening as it requires extensive sample preparation followed by a time-consuming chromatography run. This adds time and training requirements to the procedure as well as cost.

Ambient ionization techniques like desorption electrospray ionization (DESI) or direct analysis in real time (DART) offer a rapid and direct means to analyze complex samples. The sample just needs to be positioned in front of a mass spectrometer inlet and ionized for rapid analysis at atmospheric pressure. These techniques are being increasingly studied for their potential use in forensic and clinical applications. The current NPS crisis requires rapid analysis of biofluids, which is more easily done using the ambient ionization technique paper spray mass spectrometry (MS). Paper spray involves a solvent extraction of a dried biofluid spot on a wedge of paper followed by electrospray from a macroscopic point and charging the paper with several thousand volts. Using paper spray MS, results for both legal and illicit substances can be acquired in minutes at low to sub-ng/mL concentration levels depending on the analyte.

A major concern with paper spray-MS is increased limits of detection due to the presence of matrix effects. Biofluids are complex matrices containing high concentrations of salts and biomolecules which are still present when the biofluid is directly analyzed. Careful selection of the paper only has a small improvement on detection limits for certain biofluids.

Alternatively, extracting analytes either through a liquid extraction of the biofluid on hydrophobic paper or solid phase extractions (SPE) using a cartridge with a built in SPE column component has been shown to lower detection limits. However, the improved performance of these cartridges come at the cost of requiring a more complex paper spray cartridge and requiring larger sample volumes than those typically collected.

Rapid ambient ionization techniques that utilize solid phase extractions aren't limited to paper spray either. Coated blade spray techniques use a bound stationary phase on metal blades to extract analytes from biofluid to achieve pg/mL detection limits for certain analytes. Preparing these blades, however, requires an offline extraction step which also increase method complexity. In addition, solid phase extraction techniques have difficulties with viscous biofluids like blood. This is because SPE extraction of whole blood normally requires extensive work such as centrifugation, protein precipitation or dilution prior to the extraction. Adding SPE to paper spray increases the complexity of the autosampler cartridge and the analysis.

SUMMARY

According to a first aspect ("Example 1"), provided herein is a mass spectrometry sample substrate including a porous material and a sesame seed or other similar oil.

According to another example ("Example 2"), the porous material of the mass spectrometry sample substrate of Example 1 is selected from cellulose filter paper, ashless filter paper, nitrocellulose filter paper, a glass microfiber filter, porous polyethylene sheets, polyvinylidene difluoride (PVDF) paper, chromatography paper, or flat materials coated with an absorbent layer made from silica gel, cellulose, alumina oxide, or other powders.

According to another example ("Example 3"), further to Example 1 or Example 2, the sesame seed oil or other similar oil is absorbed on at least a portion of the porous material.

According to another example ("Example 4"), further to any one of Examples 1-3, the sesame seed or other similar oil is absorbed to the entirety of the porous material.

According to another example ("Example 5"), further to any one of Examples 1-3, the porous material is an elongated rectangle and the sesame seed oil is absorbed to one end of the porous material.

According to another example ("Example 6"), further to any one of Examples 1-5, the porous material is a thin sheet.

According to another example ("Example 7"), further to Example 6, the porous material has a thickness of about 150 μm to about 200 μm.

According to a second aspect ("Example 8), provided herein is a method for collecting and concentrating analytes from a biological sample by contacting the mass spectrometry sample substrate of any one of Examples 1-7 with the biological sample.

According to another example ("Example 9"), further to Example 8, an edge of the mass spectrometry sample substrate is contacted with the biological sample.

According to another example ("Example 10"), further to Example 8, a volume of the biological sample is spotted on the mass spectrometry sample substrate.

According to another example ("Example 11"), further to Example 10, the volume of the biological sample is spotted on the mass spectrometry sample substrate at or near an edge or corner of the mass spectrometry sample substrate.

According to another example ("Example 12"), further to any one of Examples 8-11, the porous material is an elongated rectangle, the sesame seed oil is absorbed to one end of the porous material, and the mass spectrometry sample substrate is contacted with the biological sample at an edge of the end of the porous material to which the sesame seed oil is absorbed or the biological sample is spotted on the mass spectrometry sample substrate at the end of the porous material to which the sesame seed oil is absorbed.

According to another example ("Example 13"), further to any one of Examples 8-12, the mass spectrometry sample substrate is dried after it is contacted with the biological sample to produce a dried mass spectrometry sample.

According to another example ("Example 14"), further to Example 13, the dried mass spectrometry sample is stored.

According to another example ("Example 15"), further to Example 14, the dried mass spectrometry sample is stored for about 30 days or less.

According to another example ("Example 16"), further to Example 14 or Example 15, the dried mass spectrometry sample is stored at room temperature (18-27° C.).

According to another example ("Example 17"), further to any one of examples 8-16, the biological sample is urine, saliva, or blood.

According to another example ("Example 18"), further to any one of examples 8-17, the analytes include one or more analytes selected from a cannabinoid, a cannabinoid metabolite, a synthetic cannabinoid, and a synthetic cannabinoid metabolite.

According to another aspect ("Example 19"), provided herein is a method for storing a biological sample including one or more analytes. The method includes contacting the mass spectrometry sample substrate of any one of Examples 1-7 with the biological sample, drying the mass spectrometry sample substrate after it is contacted with the biological sample to produce a dried mass spectrometry sample, and storing the dried mass spectrometry sample.

According to another example ("Example 20"), further to Example 19, the dried mass spectrometry sample is stored at room temperature ("18-27° C.). The biological sample can be urine, saliva, or blood, and the analyte includes one or more of a cannabinoid metabolite, a synthetic cannabinoid, and a synthetic cannabinoid metabolite.

According to another aspect ("Example 21"), provided herein is a method of analyzing one or more analytes in a biological sample, the method including: securing a mass spectrometry sample substrate of any one of claims 1-7 to a paper spray tip, wherein the mass spectrometry sample substrate further comprises a biological sample; positioning the mass spectrometry sample substrate comprising the biological sample and the paper spray tip in functional proximity with a mass spectrometer; applying a volume of a solvent to the mass spectrometry sample substrate comprising the biological sample to cause one or more analytes from the biological sample to pass from the mass spectrometry sample substrate to the paper spray tip; applying an electrical potential to the paper spray tip to ionize at least a portion of the one or more analytes; and analyzing the ionized portion of the one or more analytes by mass spectrometry. The mass spectrometry sample substrate may be secured to the paper spray tip by a clip or a paper spray mass spectrometry cartridge. The paper spray mass spectrometry cartridge may include a housing and at least one conductive element, the housing comprising a bottom housing with an open end configured to accept a paper spray tip, and a top housing configured to securely engage the bottom housing. The biological sample may be, urine, saliva, or blood, and the one or more analytes may include one or more of a cannabinoid, a cannabinoid metabolite, a synthetic cannabinoid, and a synthetic cannabinoid metabolite.

According to one example ("Example 28"), a solid phase extraction (SPE) strip includes a porous material and an SPE element disposed thereon.

According to another example ("Example 29"), further to Example 28, the porous material is selected from cellulose filter paper, ashless filter paper, nitrocellulose filter paper, a glass microfiber filter, porous polyethylene sheets, polyvinylidene difluoride (PVDF) paper, chromatography paper, or flat materials coated with an absorbent layer made from silica gel, cellulose, alumina oxide, or other powders.

According to another example ("Example 30"), further to Example 28 or Example 29, the SPE element includes a polymeric, water-wettable, reverse phase-type SPE powder.

According to another example ("Example 31"), further to any one of Examples 28-30, the SPE element includes an SPE powder and a binder.

According to another example ("Example 32"), further to Example 31, the binder is corn starch.

According to another example ("Example 33"), further to Example 31 or Example 32, the binder is present in the SPE element at a concentration of about 0.5% by mass to about 10% by mass.

According to another example ("Example 34"), further to any one of Examples 28-33, the porous material is an elongated rectangle and the SPE element is approximately square and disposed on one end of the porous material.

According to another example ("Example 35"), further to Example 34, the approximately square SPE element has a width approximately equal to a width of the porous material.

According to another example ("Example 36"), further to any one of Examples 28-35, the SPE strip further comprising a reinforcing element disposed atop the SPE element, wherein the reinforcing element has approximately the same dimensions as a surface of the SPE element and comprises filter paper or chromatographic paper.

According to another example ("Example 37"), further to any one of Examples 38-33 or 36, the porous material includes a first section and a second section, wherein the first section is wider than the second section, the second section extends outwardly from one edge of the first section, and the SPE element is disposed on the second section.

According to another example ("Example 38"), further to Example 37, the second section is approximately square.

According to another example ("Example 39"), further to Example 37 or Example 38, the SPE element has a width approximately equal to a width of the second section.

According to another example ("Example 40"), further to any one of Examples 28-39, the SPE strip includes a support layer positioned at a surface of the porous material opposite to that on which the SPE element is disposed.

According to another example ("Example 41"), further to Example 40, the support layer has approximately the same dimensions as the porous material, or is larger than the porous material.

According to another example ("Example 42"), further to Example 40 or Example 41, the support layer is a plastic sheet or film selected from Derlin and acetal.

According to another example ("Example 43"), further to any one of Examples 28-42, the porous material is a thin sheet.

According to another example ("Example 44"), further to Example 43, the porous material has a thickness of about 150 μm to about 200 μm.

According to one example ("Example 45"), a method for collecting and concentrating analytes from a biological sample includes contacting the SPE element of the SPE strip of any one of Examples 28-44 with the biological sample.

According to another example ("Example 46"), further to Example 45, a volume of the biological sample is applied to the SPE element.

According to another example ("Example 47"), further to Example 45 or Example 46, the method includes drying the SPE strip after the SPE element it is contacted with the biological sample to produce a dried SPE sample strip According to another example ("Example 48"), further to Example 47, the method includes washing the SPE element after drying with highly purified water and drying the washed SPE element.

According to another example ("Example 49"), further to Example 47 or Example 48, the method includes storing the dried SPE sample strip.

According to another example ("Example 50"), further to Example 49, the dried SPE sample strip is stored for about 30 days or less.

According to another example ("Example 51"), further to Example 49 or Example 50, the dried SPE sample strip is stored at about 18° C.-27° C.

According to another example ("Example 52"), further to any one of Examples 45-51, the biological sample is urine, saliva, or plasma.

According to another example ("Example 53"), further to any one of Examples 45-52, the analytes include one or more analytes selected from: fentanyl, a fentanyl metabolite, a synthetic cannabinoid, a synthetic cannabinoid metabolite, a synthetic psychedelic tryptamine, a synthetic psychedelic tryptamine metabolite, a psychedelic phenethylamine, and a psychedelic phenethylamine metabolite.

According to one example ("Example 54"), a method for storing a biological sample including one or more analytes includes contacting the SPE element of the SPE strip of any one of claims 28-44 with the biological sample, drying the SPE strip after it is contacted with the biological sample to produce a dried SPE sample strip, and storing the dried SPE sample strip.

According to another example ("Example 55"), further to Example 54, the dried mass spectrometry sample is stored at about 18° C.-27° C.

According to another example ("Example 56"), further to Example 54 or Example 55, the biological sample is urine, saliva, or plasma.

According to another example ("Example 57"), further to any one of Examples 54-56, the one or more analytes is selected from: fentanyl, a fentanyl metabolite, a synthetic cannabinoid, a synthetic cannabinoid metabolite, a synthetic psychedelic tryptamine, a synthetic psychedelic tryptamine metabolite, a psychedelic phenethylamine, and a psychedelic phenethylamine metabolite.

According to one example ("Example 58"), a method of analyzing one or more analytes in a biological sample includes: securing the SPE element of the SPE strip of any one of Examples 28-44 to a paper spray tip, wherein the SPE element comprises the biological sample and/or analytes from the biological sample; positioning the SPE element comprising the biological sample and/or analytes from the biological sample, and the paper spray tip in functional proximity with a mass spectrometer; applying a volume of a solvent to the SPE element comprising the biological sample and/or analytes from the biological sample to cause one or more analytes from the biological sample to pass from the SPE element to the paper spray tip; applying an electrical potential to the paper spray tip to ionize at least a portion of the one or more analytes; and analyzing the ionized portion of the one or more analytes by mass spectrometry.

According to another example ("Example 59"), further to Example 58, the SPE element is secured to the paper spray tip by a clip or a paper spray mass spectrometry cartridge.

According to another example ("Example 60"), further to Example 58 or Example 59, the biological sample is selected from urine, saliva, and plasma.

According to another example ("Example 61"), further to any one of Examples 58-60, the one or more analytes is selected from: fentanyl, a fentanyl metabolite, a synthetic cannabinoid, a synthetic cannabinoid metabolite, a synthetic psychedelic tryptamine, a synthetic psychedelic tryptamine metabolite, a psychedelic phenethylamine, and a psychedelic phenethylamine metabolite.

According to one example ("Example 62"), a paper spray mass spectrometry cartridge is configured to accept the SPE strip of any one of Examples 28-44 and to retain the SPE element against a paper spray tip.

According to another example ("Example 63"), further to Example 62, a majority of the SPE strip is removed from the paper spray mass spectrometry cartridge, leaving the SPE element and any porous material associated therewith within the paper spray mass spectrometry cartridge.

According to one example ("Example 64"), a paper spray mass spectrometry cartridge includes a solvent well and a solid phase extraction (SPE) element disposed within the solvent well.

According to another example ("Example 65"), further to Example 64, the SPE element comprises a polymeric, water-wettable, reverse phase-type SPE powder.

According to another example ("Example 66"), further to Example 64 or Example 65, the SPE element comprises an SPE powder and a binder.

According to another example ("Example 67"), further to Example 66, the binder is corn starch.

According to another example ("Example 68"), further to Example 66 or Example 67, the binder is present in the SPE element at a concentration of about 0.5% by mass to about 10% by mass.

According to one example ("Example 69"), a method for collecting and concentrating analytes from a biological sample includes contacting the SPE element of the paper spray mass spectrometry cartridge of any one of Examples 64-68.

According to another example ("Example 70"), further to Example 69, a volume of the biological sample is deposited in the solvent well.

According to another example ("Example 71"), further to Example 69 or Example 70, the method includes positioning a wicking pad below the solvent well having the SPE element deposited therein.

According to another example ("Example 72"), further to any one of Examples 69-71, the method includes drying the SPE element after it is contacted with the biological sample to produce a dried SPE sample element.

According to another example ("Example 73"), further to Example 72, the method includes washing the SPE element after drying with highly purified water and drying the washed SPE element.

According to another example ("Example 74"), further to Example 72 or Example 73, the method includes storing the paper spray mass spectrometry cartridge having the dried SPE sample element.

According to another example ("Example 75"), further to Example 74, the paper spray mass spectrometry cartridge having the dried SPE sample element is stored for about 30 days or less.

According to another example ("Example 76"), further to Example 74 or Example 75, the paper spray mass spectrometry cartridge having the dried SPE sample element is stored at about 18° C.-27° C.

According to another example ("Example 77") further to any one of Examples 69-76, the biological sample is urine, saliva, plasma, or whole blood.

According to another example ("Example 78"), further to any one of Examples 69-77, the analytes include one or more analytes selected from: fentanyl, a fentanyl metabolite, a synthetic cannabinoid, a synthetic cannabinoid metabolite, a synthetic psychedelic tryptamine, a synthetic psychedelic tryptamine metabolite, a psychedelic phenethylamine, and a psychedelic phenethylamine metabolite.

According to one example ("Example 79"), a method of analyzing one or more analytes in a biological sample includes: positioning the SPE element of the paper spray mass spectrometry cartridges of any one of Examples 64-68 above a paper spray tip, wherein the SPE element comprises the biological sample and/or analytes from the biological sample; positioning the paper spray tip in functional proximity with a mass spectrometer; applying a volume of a solvent to the solvent well to cause one or more analytes from the biological sample to pass from the SPE element to the paper spray tip; applying an electrical potential to the paper spray tip to ionize at least a portion of the one or more analytes; and analyzing the ionized portion of the one or more analytes by mass spectrometry.

According to another example ("Example 80"), further to Example 79, the biological sample is selected from urine, saliva, plasma, and whole blood.

According to another example ("Example 81"), further to Example 79 or Example 80, the one or more analytes is selected from: fentanyl, a fentanyl metabolite, a synthetic cannabinoid, a synthetic cannabinoid metabolite, a synthetic psychedelic tryptamine, a synthetic psychedelic tryptamine metabolite, a psychedelic phenethylamine, and a psychedelic phenethylamine metabolite.

BRIEF DESCRIPTION OF THE DRAWINGS

The features and objects of this disclosure, and the manner of attaining them, will become more apparent and the disclosure itself will be better understood by reference to the accompanying drawings, wherein.

Figure 6A:
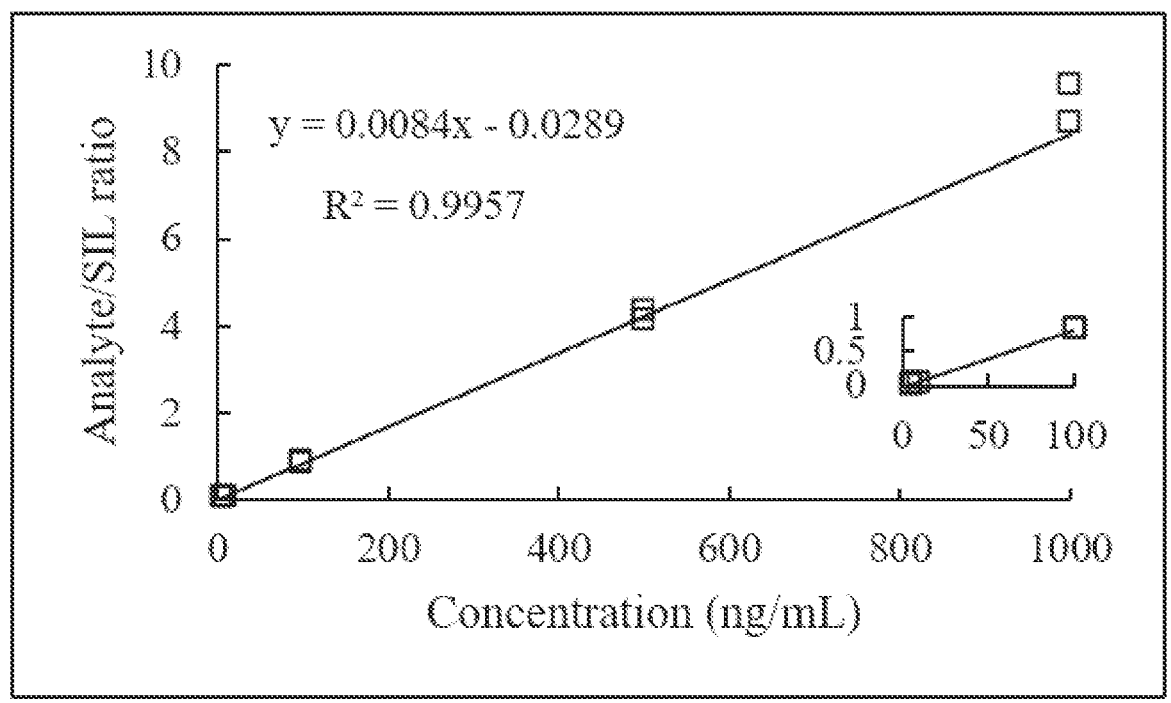
FIGS. 6A-6D depict calibration curves for THC after 1 day (FIGS. 6A and 6C) and after 27 days (FIGS. 6B and 6D)
Figure 6B:
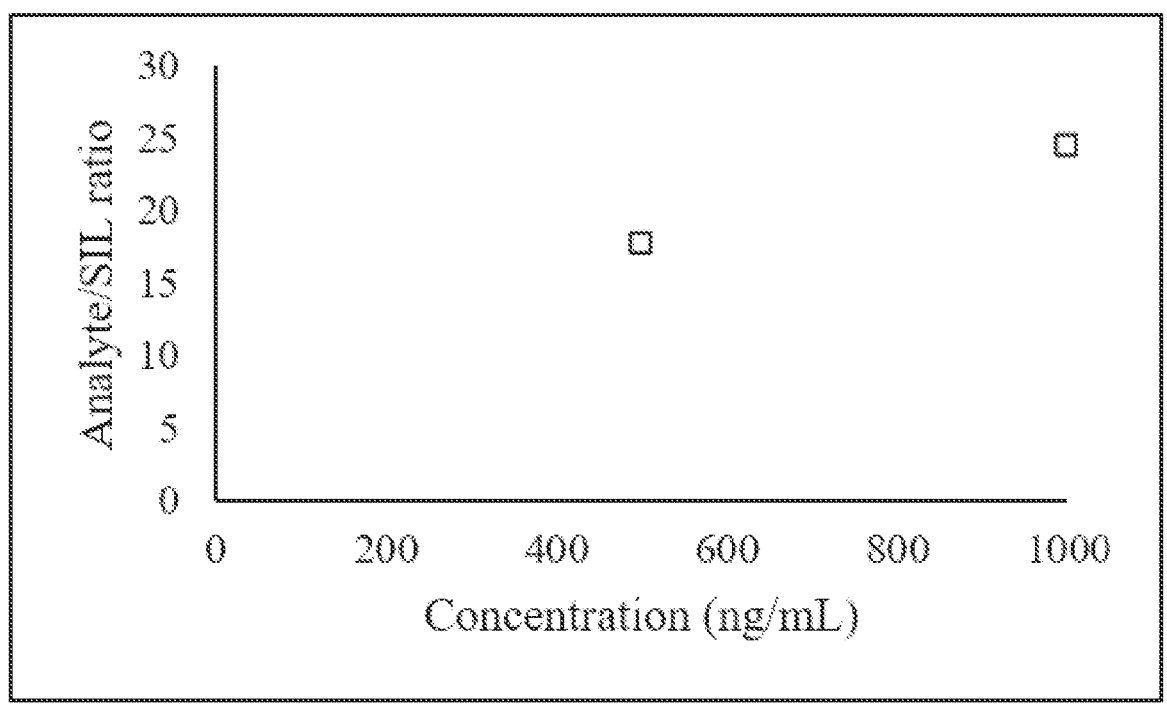
Figure 6C:
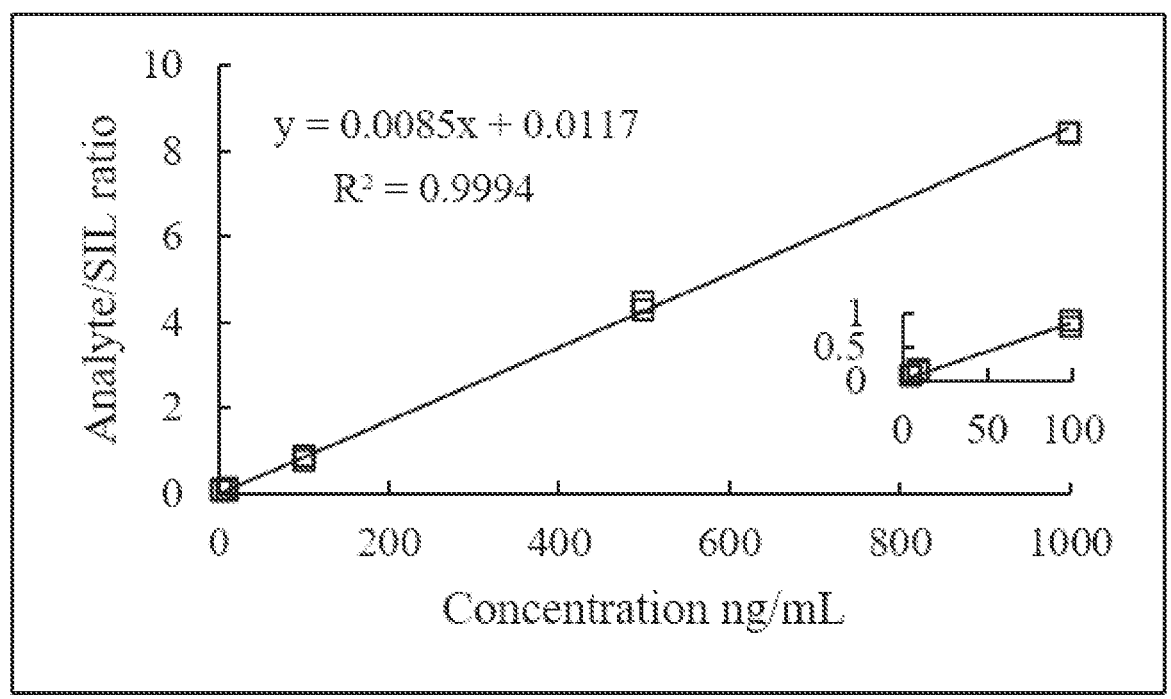
Figure 6D:
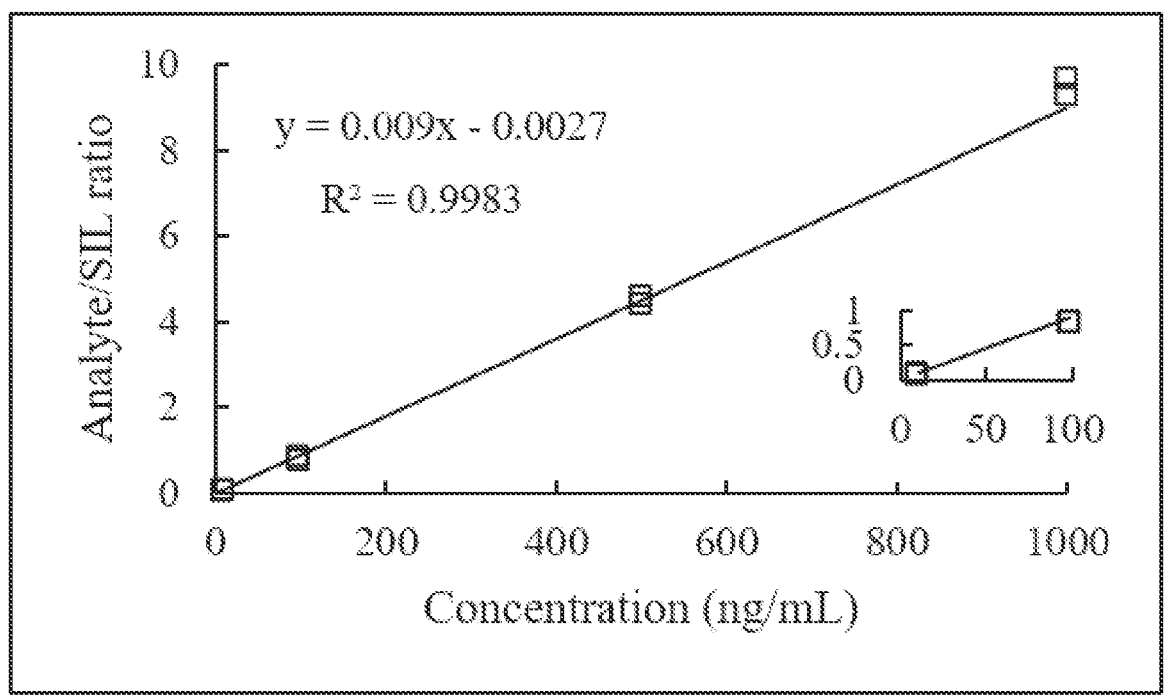
Figure 7A:
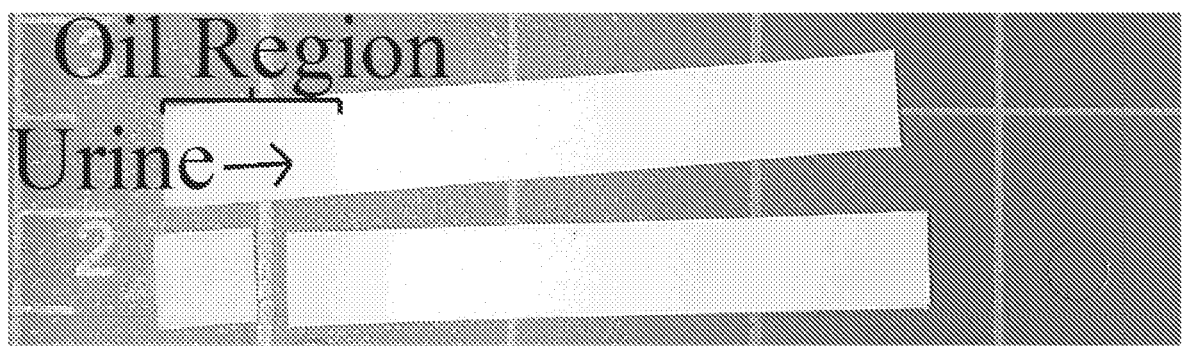
Figure 7B:
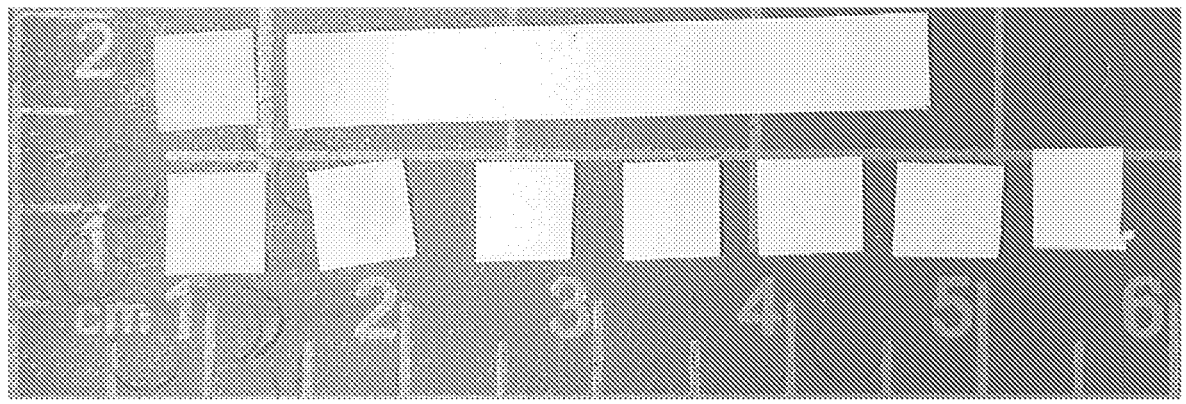
Figure 8:
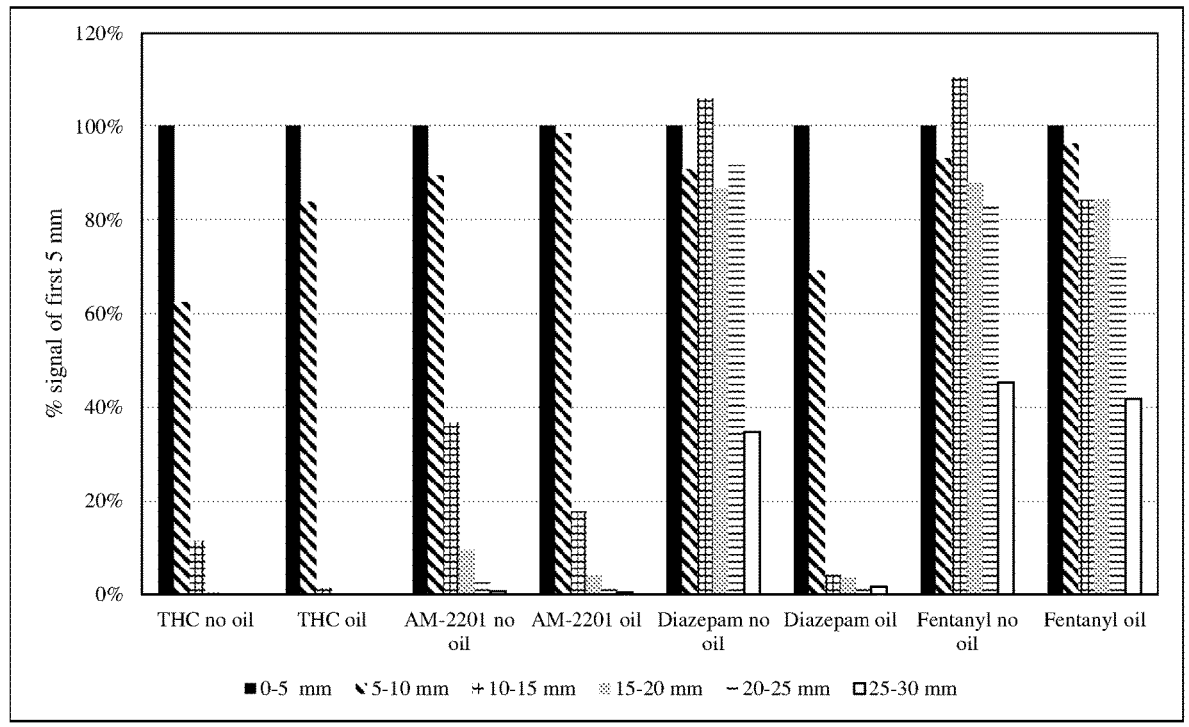
Figures 9A, 9B:
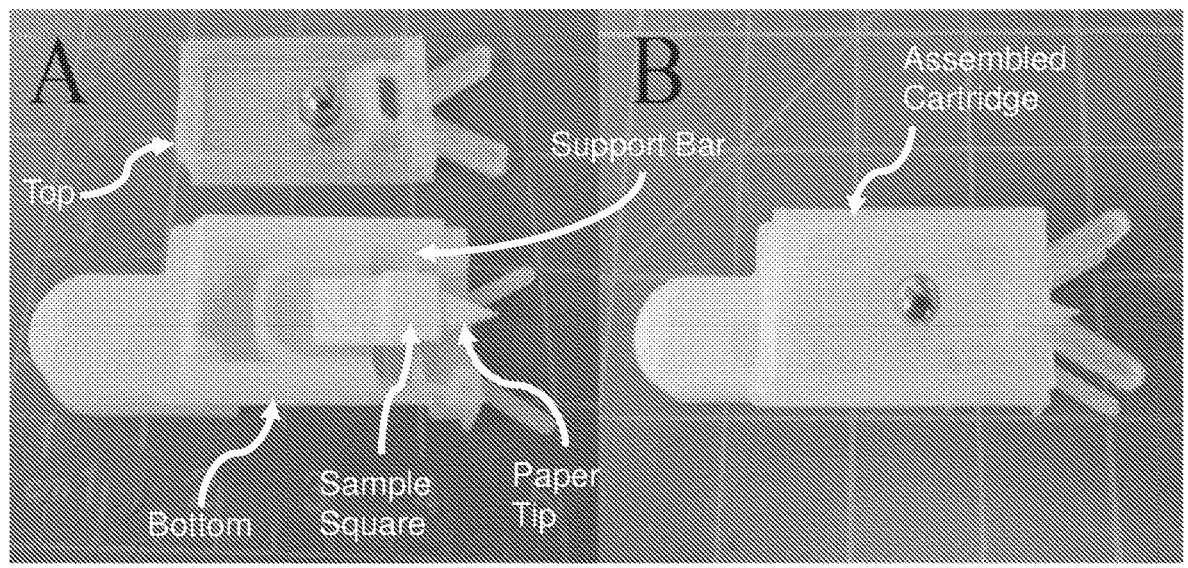

of sample storage using paper strip extraction without sesame seed oil (FIGS. 6A and 6B) and with sesame seed oil (FIGS. 6C and 6D);

FIG. 7A is a photograph depicting a mass spectrometry sample substrate onto which a urine sample has been deposited according to an embodiment;

FIG. 7B is a photograph depicting a mass spectrometry sample substrate onto which a urine sample has been deposited according to an embodiment, and the mass spectrometry sample has been divided into 5 mm×5 mm section;

FIG. 8 is a bar graph illustrating analyte concentrations throughout a porous material with (mass spectrometry sample substrate) or without sesame seed oil; and FIG. 9A is a photograph of a mass spectrometry cartridge according to an embodiment, prior to assembly;

FIG. 9B is a photograph of an assembled mass spectrometry cartridge according to an embodiment.

Figure 10A:
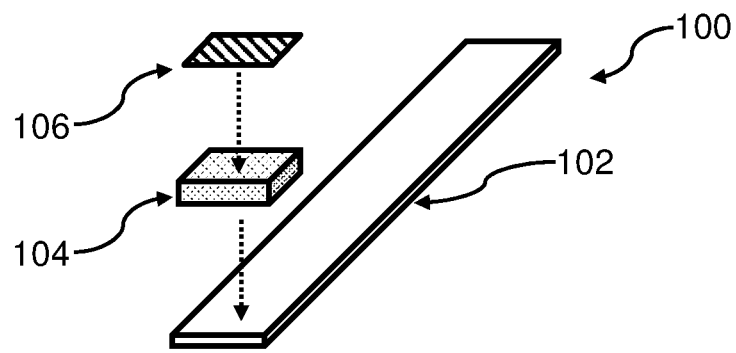
Figure 10B:
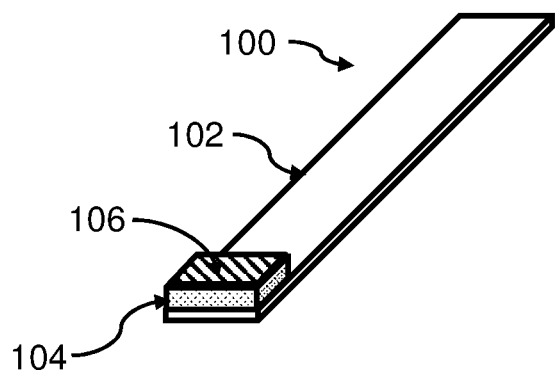
Figure 10C:
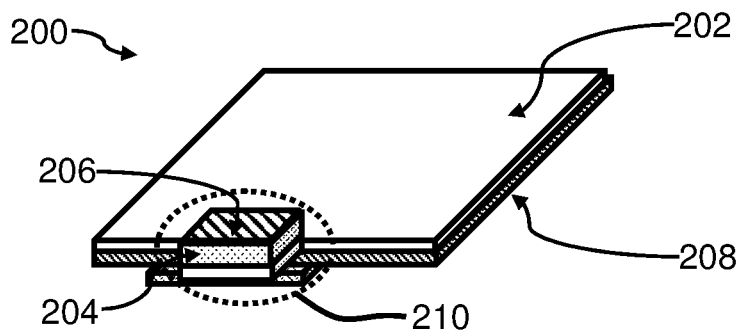
Figure 11A:
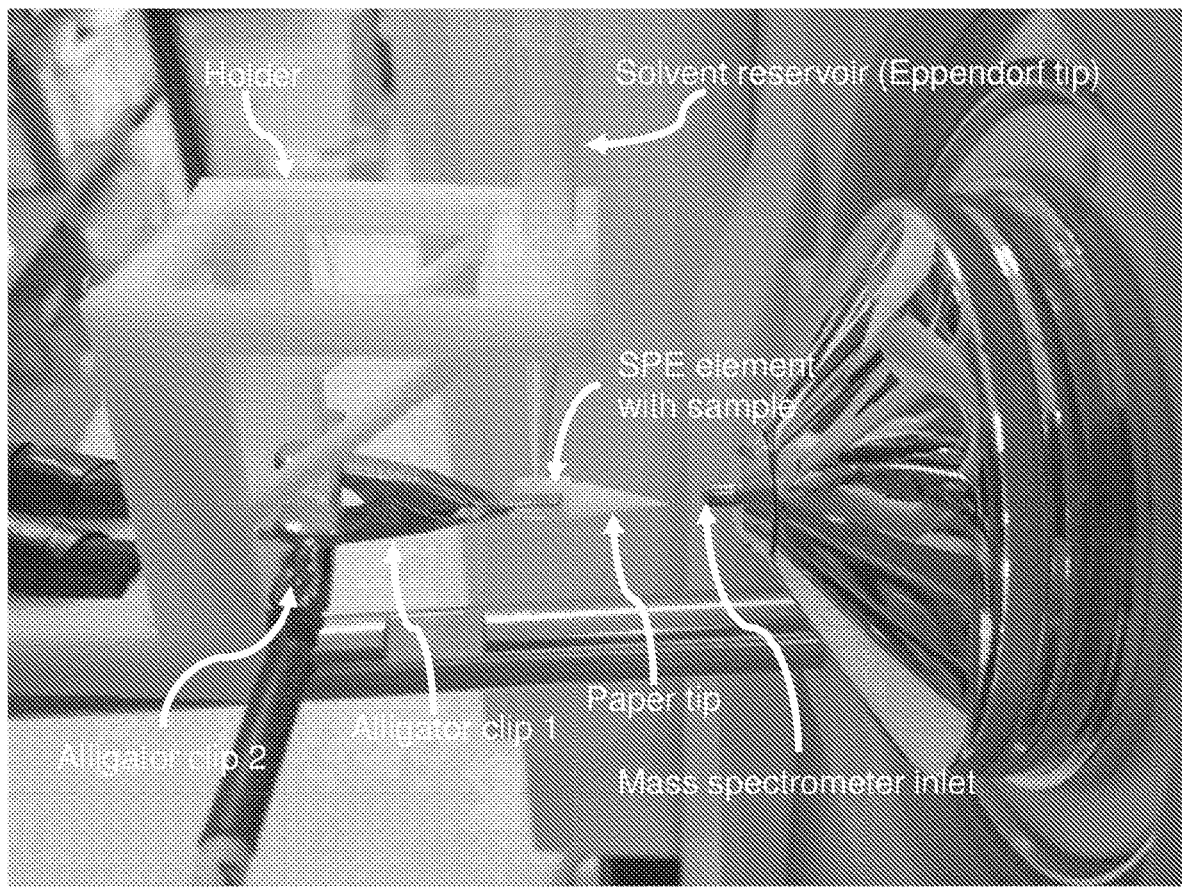
Figure 11B:
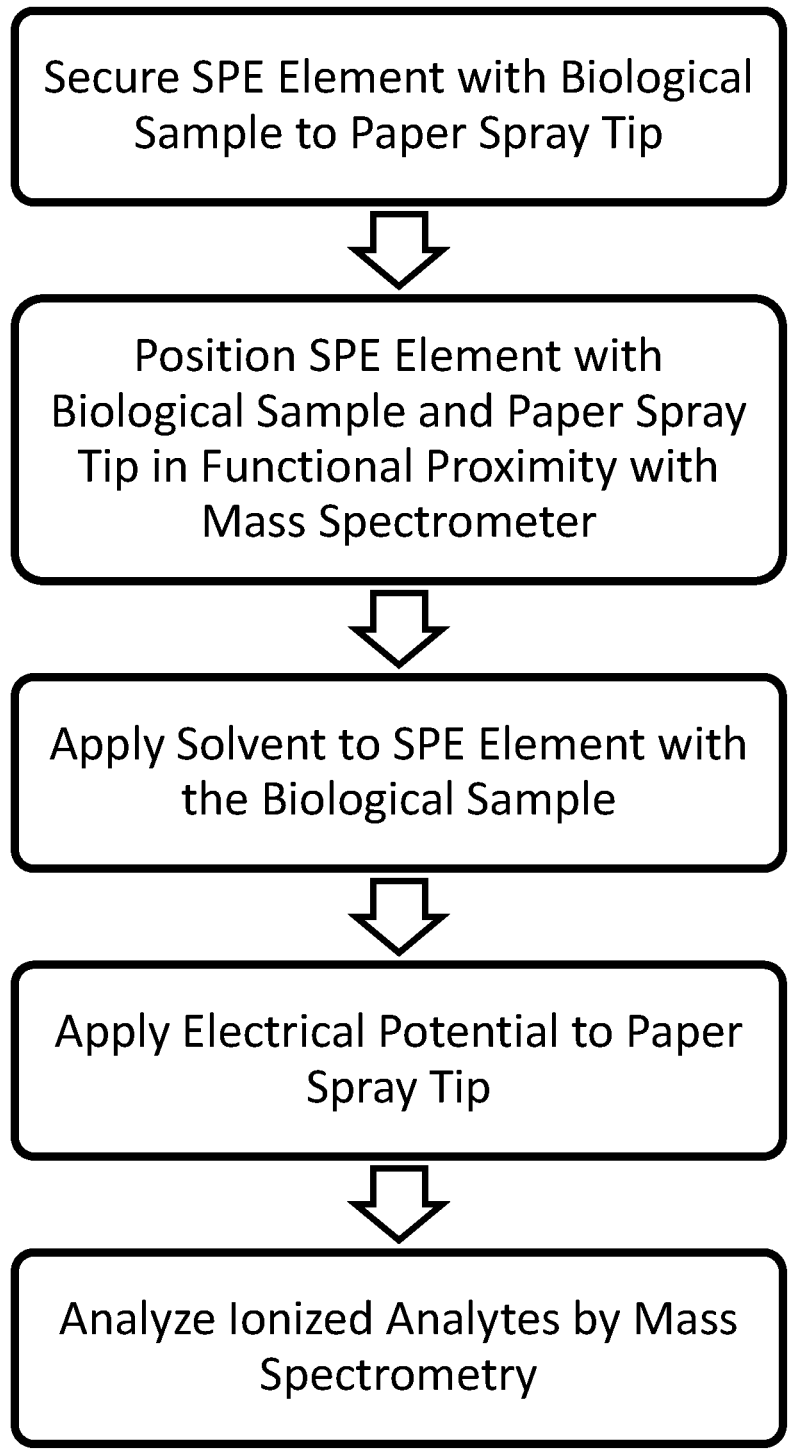
Figures 12A, 12B:
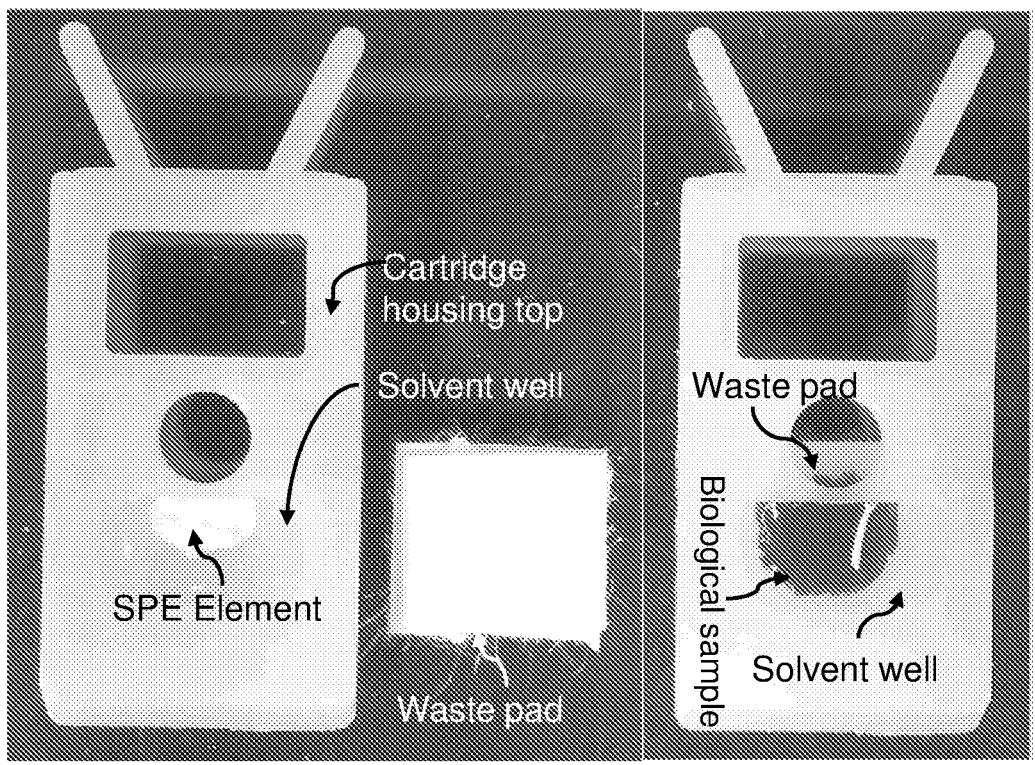
Figures 12C, 12D:
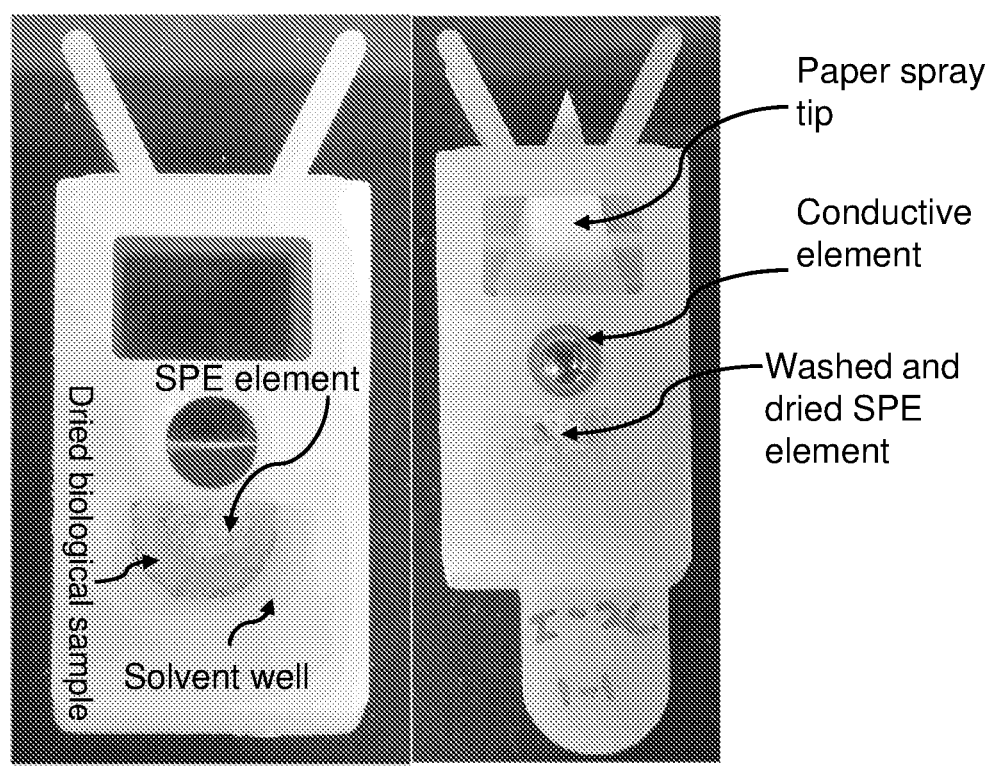
Figure 13A:
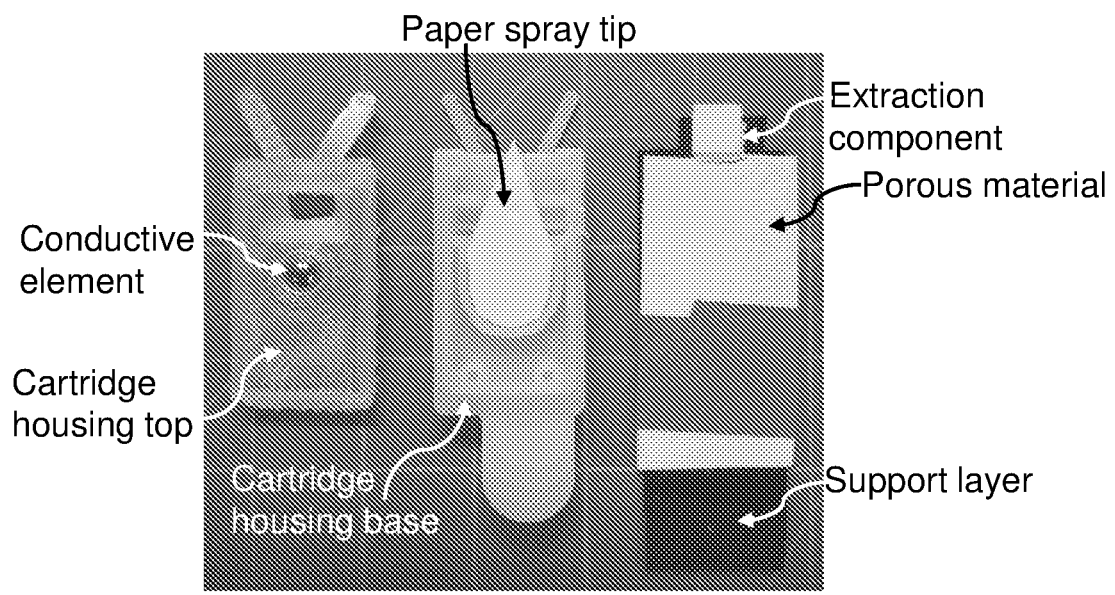
Figure 13B:
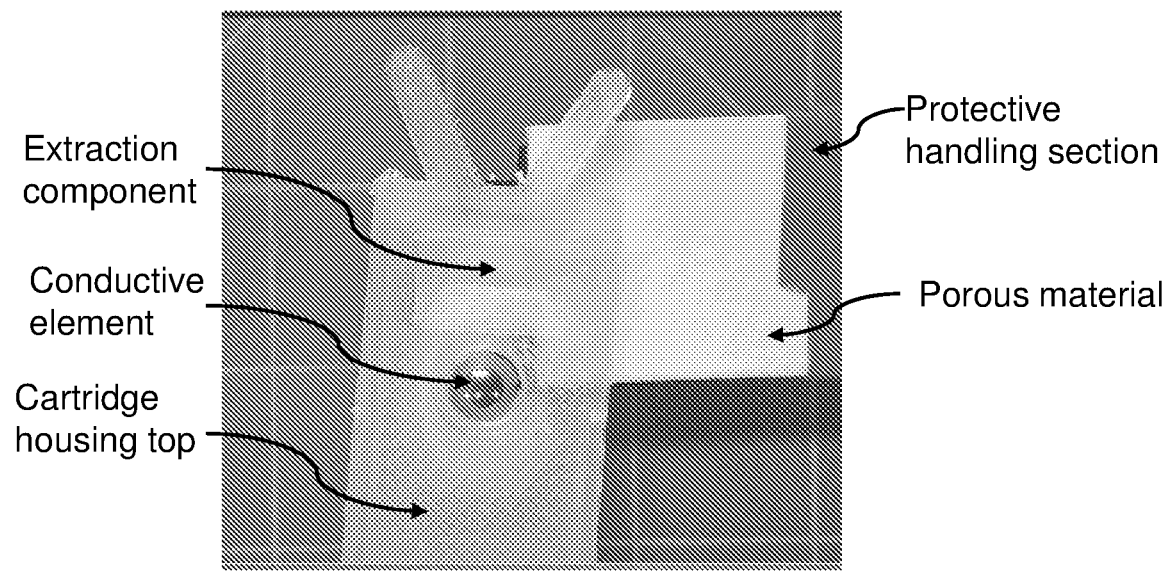
Figure 13C:
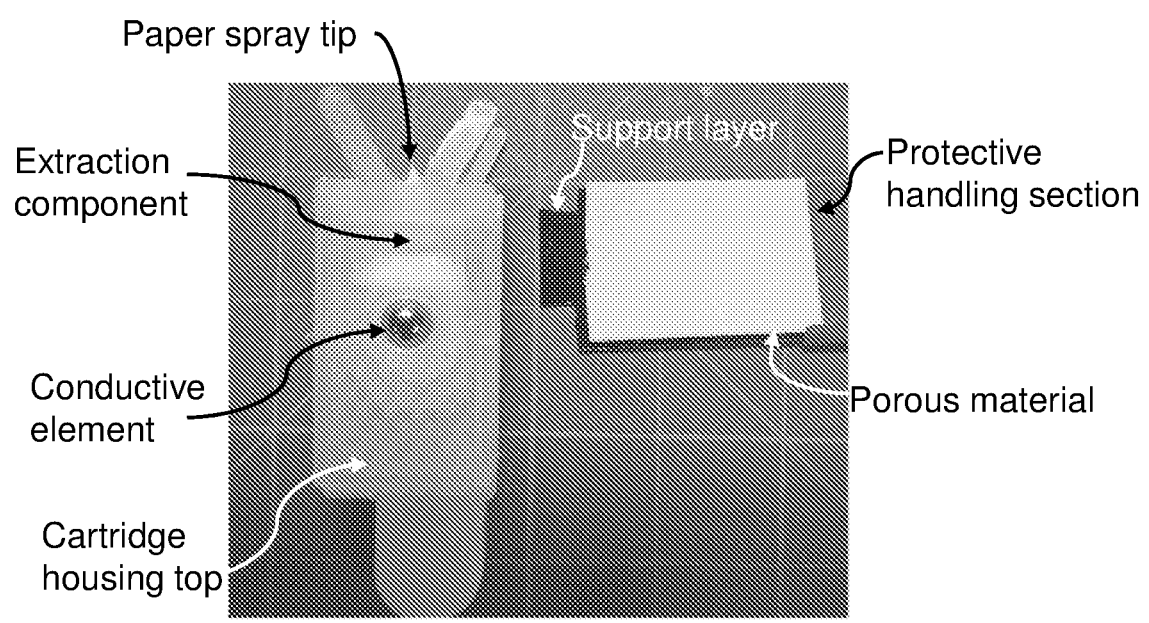
Figure 14A:
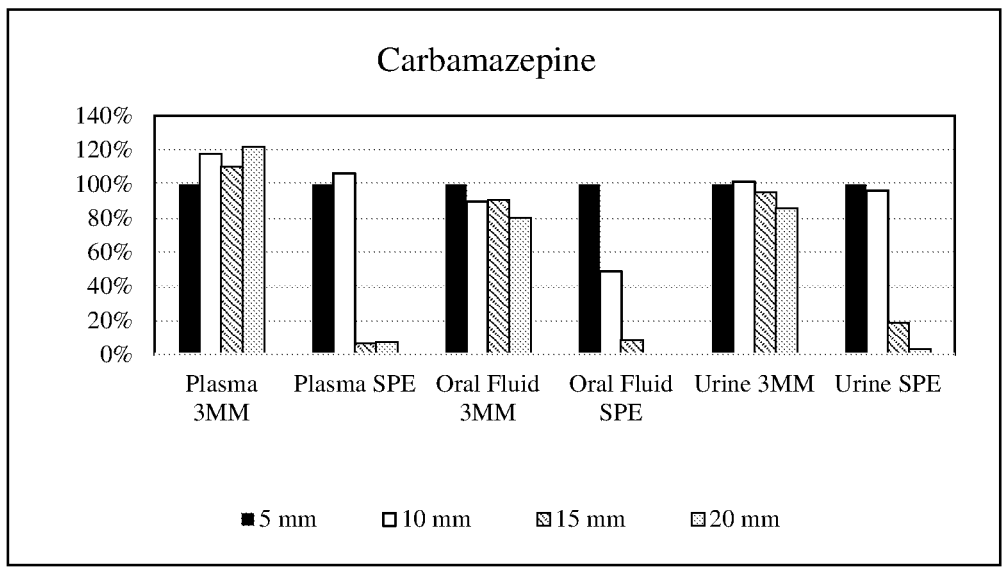
Figure 14B:
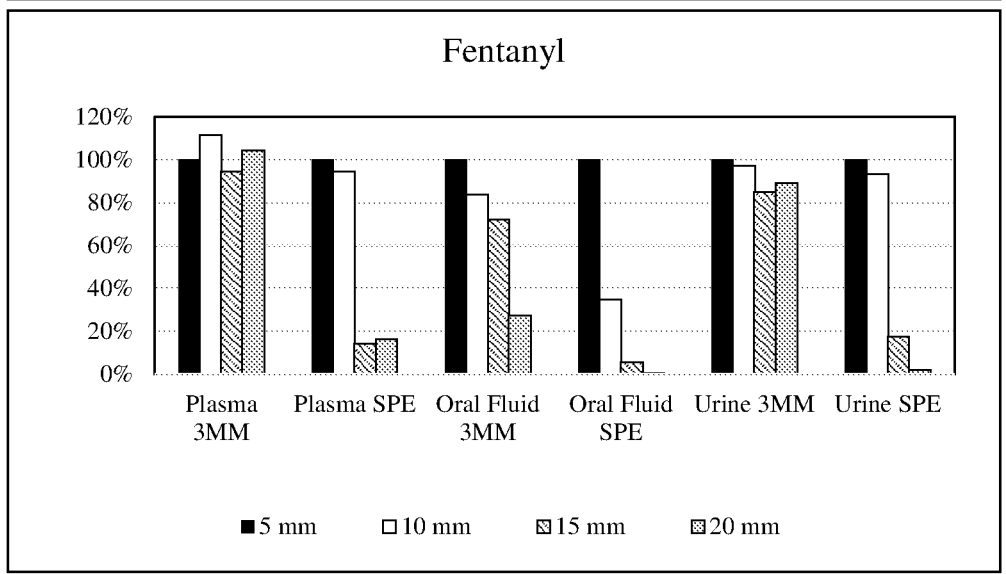
Figure 14C:
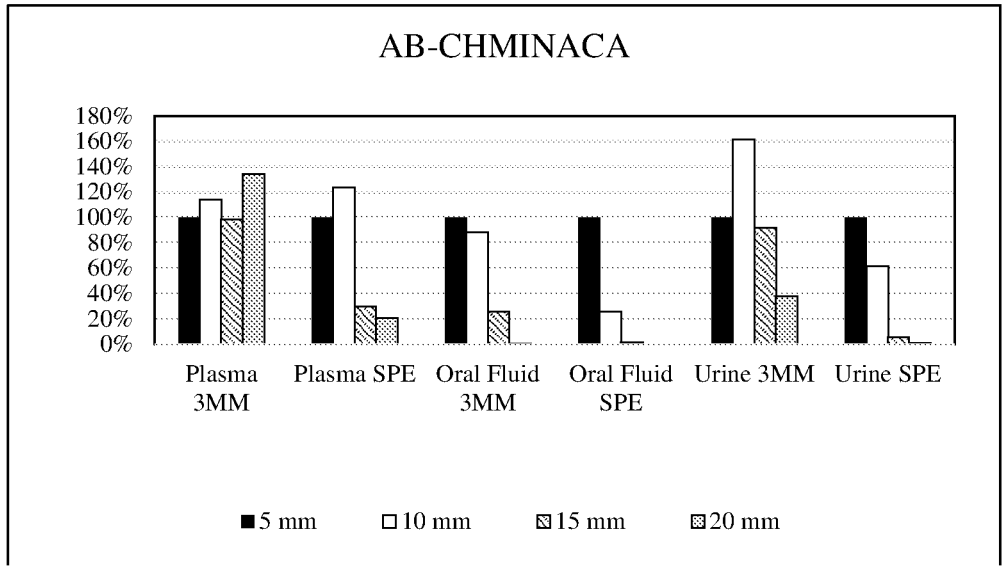

FIG. 10A illustrates the elements of a solid phase extraction strip in an exploded view according to an embodiment;

FIG. 10B illustrates a solid phase extraction strip according to an embodiment;

FIG. 10C illustrates a solid phase extraction strip according to another embodiment;

FIG. 11A is a photograph depicting the analysis of a solid phase extraction strip by paper spray mass spectrometry FIG. 11B is a flow chart presenting select steps of a method of analyzing one or more analytes in a biological sample according to an embodiment;

FIG. 12A is a photograph of a top half of a solid phase extraction autosampler cartridge according to an embodiment;

FIG. 12B is a photograph depicting whole blood flowing through the solid phase extraction element to a waste pad of a solid phase extraction autosampler cartridge according to an embodiment;

FIG. 12C is a photograph depicting dried whole blood sample in the solid phase extraction element of a solid phase extraction autosampler cartridge according to an embodiment;

FIG. 12D is a photograph of an assembled solid phase extraction autosampler cartridge following a wash step according to an embodiment;

FIG. 13A is a photograph of the components of an autosampler cartridge with built-in solid phase extraction strip extraction according to an embodiment;

FIG. 13B is a photograph of the assembled components depicted in FIG. 3A, with the solid phase extraction strip inserted into the autosampler cartridge according to an embodiment;

FIG. 13C is a photograph of the autosampler cartridge of FIG. 4B following removal of the waste strip from the autosampler cartridge according to an embodiment;

FIG. 14A is a bar graph indicating change in relative concentration of carbazepine in three biofluids over the first 20 mm of a strip of 3MM chromatography paper with and without SPE on the first 5 mm;

FIG. 14B is a bar graph indicating change in relative concentration of fentanyl in three biofluids over the first 20 mm of a strip of 3MM chromatography paper with and without SPE on the first 5 mm; and FIG. 14C is a bar graph indicating change in relative concentration of AB-CHMINACA in three biofluids over the first 20 mm of a strip of 3MM chromatography paper with and without SPE on the first 5 mm.

Although the drawings represent embodiments of the present disclosure, the drawings are not necessarily to scale and certain features may be exaggerated in order to better illustrate and explain the present disclosure. The exemplification set out herein illustrates certain embodiments of the disclosure, in various forms, and such exemplifications are not to be construed as limiting the scope of the disclosure in any manner.

DETAILED DESCRIPTION

The embodiments disclosed below are not intended to be exhaustive or limit the disclosure to the precise form disclosed in the following detailed description. Rather, the embodiments are chosen and described so that others skilled in the art may utilize its teachings.

As the terms are used herein with respect to ranges, "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Disclosed herein are mass spectrometry sample substrates. The mass spectrometry sample substrates of the present disclosure can be used in paper spray mass spectrometry to detect and quantify one or more analytes present in a biological sample. The mass spectrometry sample substrates can also be used solely for the preservation of labile cannabinoids for subsequent extraction and detection by other methods known in the field such as high-performance liquid chromatography-mass spectrometry. Also disclosed are methods for collecting and concentrating one or more analytes from a biological sample, as well as for storing a biological sample that includes one or more analytes. Methods for analyzing the one or more analytes from the biological sample, and paper spray mass spectrometry cartridges are also provided.

Mass Spectrometry Sample Substrates

In one aspect, mass spectrometry sample substrates are provided. In some embodiments, a mass spectrometry sample substrate includes a porous material and a sesame seed oil. In some embodiments, the porous material is a thin sheet. In certain embodiments, the porous material is paper. In some embodiments, the porous material has a thickness of about 100 μm to about 700 μm. In particular embodiments, the porous material has a thickness of about 150 μm to about 200 μm. The porous material can be, for example, filter paper, chromatographic paper, or any other porous, water-wettable material.

In some embodiments, the porous material is cellulose filter paper, ashless filter paper, nitrocellulose filter paper, a glass microfiber filter, porous polyethylene sheets, polyvinylidene difluoride (PVDF) paper, or chromatography paper. Other porous materials are also considered such as flat materials coated with a layer of absorbent material such as silica gel, cellulose powder, or alumina oxide. In certain embodiments, the porous material is a general-purpose cellulose filter paper, a qualitative cellulose filter paper, a quantitative ashless cellulose filter paper, a quantitative hardened ashless cellulose filter paper, or a wet strengthened filter paper. Examples of general purpose cellulose filter papers include, but are not limited to Grade 0858, Grade 0903, Grade 201 qualitative, Grade 202 qualitative, Grade 226 qualitative, Grade 2589 A, and Grade 520 a filter papers. Examples of qualitative cellulose filter papers include, but are not limited to Grade 1, Grade 2, Grade 3, Grade 4, Grade 5, Grade 6, Grade 588, Grade 591, Grade 595, Grade 597, Grade 597 L, Grade 598, Grade 602 h, and Grade 602EH qualitative filter papers. Examples of quantitative hardened ashless cellulose filter papers include, but are not limited to Grade 589/3, Grade 40, Grade 41, Grade 42, Grade 43, and Grade 44 quantitative ashless filter papers. Examples of quantitative hardened ashless cellulose filter papers include, but are not limited to Grade 540, Grade 541, and Grade 542 hardened ashless cellulose filter papers. Examples of wet strengthened cellulose filter papers include, but are not limited to Grade 113, Grade 114, Grade 1573, Grade 1575, Grade 91, and Grade 93 qualitative wet strengthened filter papers. Examples of chromatographic paper includes, but are not limited to Grade 1 Chr, Grade 17 Chr, Grade 2 Chr, Grade 20 Chr, Grade 2668 Chr, Grade 2727 Chr, Grade 3 Chr, Grade 31ET Chr, Grade 3MM, Grade 4 Chr, and Grade 54 SFC cellulose chromatography papers. In certain embodiments, the porous material is Grade 31ET Chr cellulose chromatography paper. In other embodiments, the porous material is Grade 3MM Chr cellulose chromatography paper. The filter papers provided as examples above are Whatman filters, available from GE Healthcare Lifesciences, although filter papers from other manufacturers having similar properties to those listed above are also considered.

Those of skill in the art will be able to select an appropriate porous material for use in the mass spectrometry sample substrate and related methods described herein. Parameters that influence a filter's effectiveness and appropriateness for a particular use include, but are not limited to pore size and particulate retention, adsorption, pH, surface properties, thickness, and wet strength.

Mass spectrometry sample substrates of the present disclosure include a sesame seed oil. In certain embodiments, the sesame seed oil is absorbed on to the porous material. In other embodiments, the sesame seed oil is impregnated into the porous material. When absorbed on to the porous material, a small amount of oil is spotted or otherwise applied to the surface of the porous material. When impregnated into the porous material, the porous material is saturated or nearly saturated with the oil. Care must be taken to ensure the strength of the porous material is sufficient to withstand impregnation with the sesame seed oil.

Figure 1A:
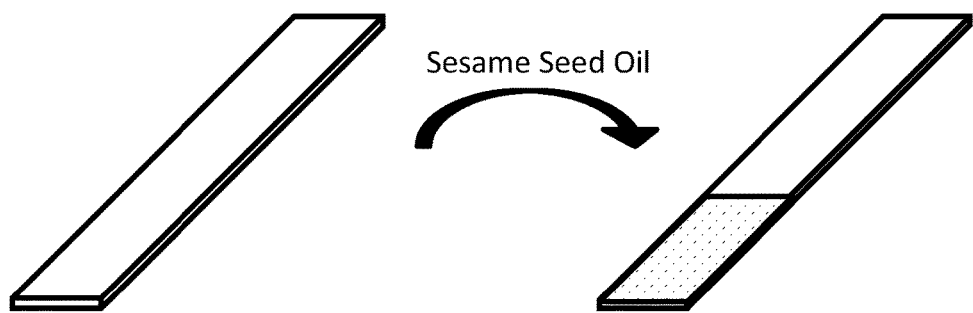
FIG. 1A illustrates the addition of sesame seed oil to a portion of a porous material to produce a mass spectrometry sample substrate according to an embodiment.
Figure 1B:
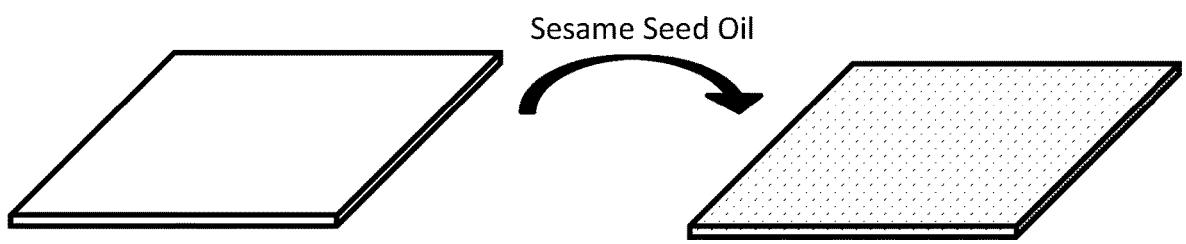
FIG. 1B illustrates the addition of sesame seed oil to the entirety of a porous material to produce a mass spectrometry sample substrate according to an embodiment.

As depicted by FIG. 1A, in some embodiments, only a portion of the porous material retains sesame seed oil. That is, sesame seed oil is absorbed on to or impregnated into only a portion of the porous material. By way of example, where only a portion of a porous material having the dimensions of about 5 mm×40 mm is to retain sesame seed oil, 2.5 µl of sesame seed oil is spotted at one end of the strip of porous material. In other embodiments, the entirety of the porous material retains sesame seed oil, as illustrated by FIG. 1B. Sesame seed oil is absorbed to an entire surface of the porous material, or the entire porous material is impregnated with sesame seed oil.

Figure 2:
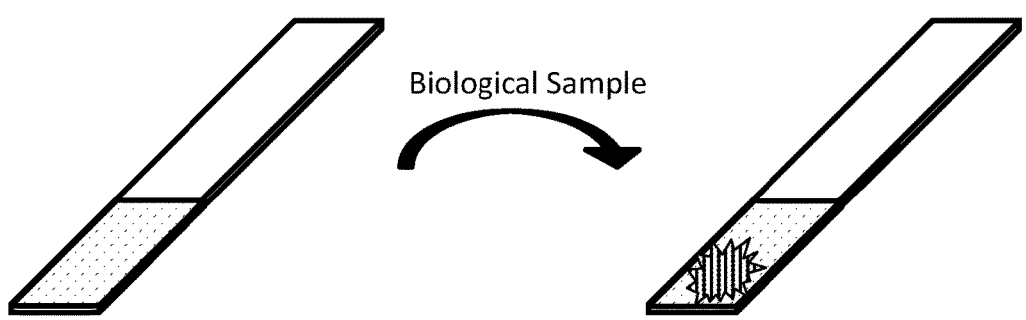
FIG. 2 illustrates the addition of a biological sample to the mass spectrometry sample of FIG. 1 according to an embodiment.

In certain embodiments, the sesame seed oil included in the mass spectrometry sample substrate is sesame seed oil obtainable by any of the normal processes used to obtain sesame seed oil, such as cold pressing or solvent extraction. In other embodiments, other natural oils containing unsaturated fatty acids and antioxidants are placed on the mass spectrometry sample substrate. In other embodiments, the sample substrate is treated with a synthetic mixture that includes unsaturated fatty acids and antioxidant materials that mimic the properties of sesame seed oil Methods for Collecting and Concentrating Analytes from a Biological Sample In another aspect, provided herein are methods for collecting and concentrating analytes from a biological sample. In some embodiments, such methods include contacting a mass spectrometry sample substrate described herein with a biological sample. In certain embodiments, the biological sample is one of urine, saliva, and blood. The mass spectrometry sample substrate can be contacted with the biological sample by, for example, touching an edge of the mass spectrometry sample substrate to the biological sample, or by spotting a volume of the biological sample onto the mass spectrometry sample substrate. In some embodiments, an edge at an end of a mass spectrometry sample substrate is contacted with the biological sample. For example, for a mass spectrometry sample substrate having the dimensions of 5 mm×40 mm, one of the 5 mm edges is contacted with the biological sample. In other embodiments, the biological sample is spotted onto the mass spectrometry sample substrate near one of its ends, as illustrated by FIG. 2. In yet other embodiments, the biological sample is spotted onto the spectrometry sample substrate approximately centrally. Preferably, the biological sample is contacted with a portion or section of the mass spectrometry sample substrate that includes the sesame seed oil. In an embodiment, the mass spectrometry sample substrate includes an elongated rectangular porous material including sesame seed oil at one end of the elongated rectangular porous material (e.g., the oil is absorbed to the one end), and the mass spectrometry sample substrate is contacted with the biological sample at an edge of the end of the mass spectrometry sample substrate that include the sesame seed oil. Alternatively, the biological sample can be spotted on the mass spectrometry sample substrate at the end that includes the sesame seed oil.

Methods for collecting and concentrating analytes from a biological sample can, in some embodiments, further include drying the mass spectrometry sample substrate following contacting the substrate with the biological sample. This step results in a dried mass spectrometry sample. The dried mass spectrometry sample can be stored for up to about 45 days, preferably up to about 30 days. In some embodiments, the dried mass spectrometry sample is stored for about 30 days or less. The dried mass spectrometry sample can be stored at room temperature (about 20° C. to about 22° C.), or between about 15° C. to about 30° C. While the dried mass spectrometry sample may be stored at temperatures outside this range, it will be recognized that it is an advantage of the present disclosure that storage of the dried mass spectrometry sample does not require a temperature-controlled environment (e.g. refrigeration).

In certain embodiments, the biological sample is from an individual having consumed or otherwise ingested, or suspected of having consumed otherwise ingested, a substance including a natural and/or synthetic cannabinoid. Several analytical strategies have been employed in an attempt to develop a meaningful detection protocol for cannabinoids and synthetic cannabinoids, including, for example, gas chromatography-mass spectrometry (GC-MS), liquid chromatography-mass spectrometry (LC-MS), desorption electrospray ionization (DESI), direct analysis in real time (DART), and paper spray mass spectrometry. DESI, DART, and paper spray each directly analyze samples with minimal sample preparation. Paper spray, in which biological fluid samples are extracted and ionized from paper for analysis, is particularly appealing due to its low cost and short analysis time. While paper spray mass spectroscopy has been demonstrated capable of detecting certain analytes at sub-ng/ml concentrations, cannabinoids cause problems for paper spray for several reasons. For both natural and synthetic cannabinoids, the concentration in biofluids is low, and detection limits for paper spray are affected by matrix effects. This is especially problematic for THC and similar compounds, which are labile and degrade rapidly in dried spots through a number of pathways including photo and thermal degradation. Attempts to improve detection limits of paper spray have included adding a solid phase extraction component to a paper spray cartridge, performing a solvent extraction from the biofluid on top of hydrophobic paper and utilizing a membrane to filter out red blood cells from whole blood. These methods can help lower detection limits but can also increase the cost or complexity of the analysis.

The mass spectrometry sample substrates described herein offer an inexpensive and powerful means for improving cannabinoid and synthetic cannabinoid paper spray detection limits. As established by the Examples provided herein, the sesame seed oil-containing mass spectrometry sample substrates provided herein function both to preserve and concentrate certain analytes for paper spray mass spectroscopy. By flowing urine or oral fluid (i.e., saliva) through the described mass spectrometry sample substrate, synthetic and natural cannabinoids were found to concentrate at the head of the paper with the sesame seed oil (see Examples 2 and 3). THC, which is normally labile and difficult to analyze from a biofluid spot, was preserved for at least 27 days at room temperature when stored on the sesame seed oil-containing sample substrate (see Examples 1 and 3). This resulted in improved detection limits for THC to ng/ml levels in urine and oral fluid (see Example 3).

In certain embodiments, the method for collecting and concentrating analytes from a biological sample results in the collection and concentration of at least one cannabinoid, cannabinoid metabolite, synthetic cannabinoid, synthetic cannabinoid metabolite, or a combination thereof. In particular embodiments, the at least one cannabinoid includes (−)-trans-$\Delta^9$-tetrahydrocannabinol (THC). That is, the disclosed methods and sample substrates can be used to collect, concentrate, and store biological samples containing cannabinoids, cannabinoid metabolites, synthetic cannabinoids, and/or synthetic cannabinoid metabolites.

Methods for Analyzing One or More Analytes in a Biological Sample

Figure 3:
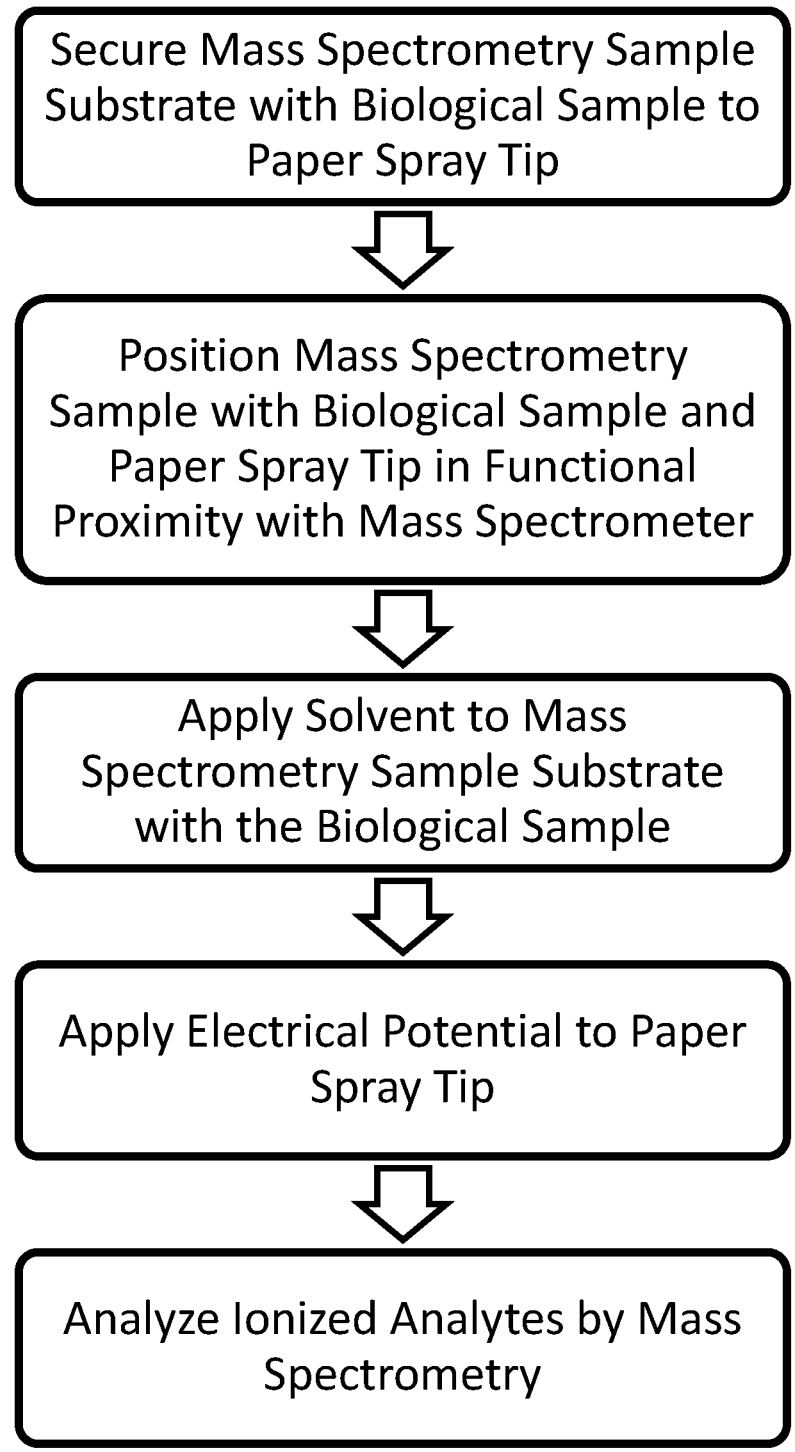
FIG. 3 a flow chart presenting select steps of a method of analyzing one or more analytes in a biological sample according to an embodiment.

In another aspect, provided herein are methods for analyzing one or more analytes in a biological sample. As illustrated by FIG. 3, in some embodiments such methods include: securing a mass spectrometry sample substrate described herein to a paper spray tip, wherein the mass spectrometry sample substrate includes a biological sample (i.e., a dried mass spectrometry sample); positioning the mass spectrometry sample substrate that includes the biological sample and the paper spray tip in functional proximity with a mass spectrometer; applying a volume of a solvent to the mass spectrometry sample substrate that includes the biological sample to cause one or more analytes from the biological sample to pass from the mass spectrometry sample substrate to the paper spray tip; applying electrical potential to the paper spray tip to ionize at least a portion of the one or more analytes; and analyzing the ionized portion of the one or more analytes by mass spectrometry. In certain embodiments, the one or more analytes include at least one cannabinoid, cannabinoid metabolite, synthetic cannabinoid, synthetic cannabinoid metabolite, or a combination thereof. In such embodiments, the methods for analyzing one or more analytes in a biological sample provide an effective, inexpensive, and easy to conduct assay for use in cases of suspected driving under the influence of drugs, particularly cannabis. With low detection limits and an ability to detect cannabinoids nearly a month after sample collection, the methods described herein provide powerful tools for law enforcement and employers.

In some embodiments, the methods for analyzing one or more analytes in a biological sample further involve including a stable isotopic label (SIL) for each analyte to be target. The SIL is added to the mass spectrometry sample substrate having the biological sample (i.e., the dried spectrometry sample) or to the paper tip before the solvent is applied to the sample substrate having the biological sample.

In certain embodiments, the mass spectrometry sample substrate is secured to the paper spray tip by a clip, a paper spray mass spectrometry cartridge, or an inert wettable binder to adhere the two substrates. The clip can be, for example, an alligator clip. In some embodiments, the clip can function to both secure the mass spectrometry sample substrate to the spray tip and to apply a voltage to the spray tip.

Mass spectrometers useful in the methods described herein are known in the art. The mass spectrometry systems are not particularly limited and can be any system that ionizes a chemical analyte and subsequently analyzes and sorts the ions based on the mass to charge ratio. Mass spectrometry systems useful in the methods described herein include, but are not limited to the Thermo Fisher Scientific Q-Exactive Focus orbitrap mass spectrometer, the Thermo® TSQ® Vantage (Thermo Finnigan), and the Sciex® Qtrap 5500 (Sciex). The mass spectrometry sample substrate comprising the biological sample and the paper spray tip are positioned in functional proximity with a mass spectrometer. That is, they are placed in a sufficient configuration to allow for the mass spectrometer to take up analyte ions generated during application of the electrical potential.

In certain embodiments, the solvent is selected to elute one or more chemical analytes from the mass spectrometry sample substrate to the paper spray tip. In an embodiment, the solvent is 80:20 acetonitrile:methanol with 25 mM sulfuric acid. The volume of solvent is sufficient to elute the one or more chemical analytes from the mass spectrometry sample substrate to the paper spray tip.

An electrical potential sufficient to ionize at least some of the one or more analytes (i.e., a portion thereof) is applied to the paper spray tip. Methods for paper spray ionization are known in the art. In some embodiments, about 3.0 to about 5.5 kV are applied to the paper spray tip for a predetermined period of time. In certain embodiments, the electrical potential is applied to the paper spray tip for about 1 minute.

Following ionization, the mass spectrometer conducts an analysis on the ionized portion of the one or more analytes and detects the identity and concentration of analytes present. In certain embodiments, the mass spectrometer detects the presence and concentration of one or more cannabinoids, cannabinoid metabolites, synthetic cannabinoids, and synthetic cannabinoid metabolites. In an embodiment, the mass spectrometer detects the presence and concentration of THC.

In certain embodiments, the methods of analyzing one or more analytes in a biological sample provided herein are automated. The mass spectroscopy sample substrates including biological sample (i.e., dried mass spectrometry sample) of the present disclosure can be incorporated into cartridges compatible with paper spray mass spectrometry systems capable of rapidly screening multiple samples.

Paper Spray Mass Spectrometry Cartridges

In one aspect, provided herein are paper spray mass spectrometry cartridges for use with a paper spray mass spectrometry system capable of rapidly screening multiple samples. In some embodiments, the paper spray mass spectrometry cartridge is configured to secure a mass spectrometry sample substrate described herein having a biological sample deposited thereon to or against a paper spray tip. The sample substrate is secured to or against the paper spray tip so that when a solvent is applied to the mass spectrometry sample substrate comprising the biological sample, one or more chemical analytes retained by the sample substrate to pass from the sample substrate to the paper spray tip. In other embodiments, the sample substrate and the paper spray tip are the same material, with the sesame seed oil, sample storage, and paper spray ionization all occurring from the same porous material. In certain embodiments, the paper spray mass spectrometry cartridge includes a housing and at least one conductive element. The housing can include a base and a top, the top configured to snap into or around the base, causing the mass spectrometry sample substrate described herein having a biological sample deposited thereon to be secured to or against the paper spray tip. The housing top further includes an opening to allow application of a solvent to the mass spectrometry sample substrate having the biological sample deposited thereon.

Solid Phase Extraction Strips

Also disclosed and described herein are solid phase extraction strips and autosampler cartridges and methods to implement solid phase extraction (SPE) with paper spray mass spectrometry. The SPE strips, autosampler cartridges, and methods of the present disclosure can be used in paper spray mass spectrometry to detect and quantify one or more analytes present in a biological sample.

In one aspect, solid phase extraction (SPE) strips are provided. Referring to FIG. 10A, an SPE strip 1000 of an embodiment includes a porous material 1002, an SPE element 1004, and optionally a reinforcing element 1006.

In certain embodiments, the porous material 1002 is a thin sheet. In some embodiments, the porous material 1002 is paper. In some embodiments, the porous material 1002 has a thickness of about 100 µm to about 700 µm. In particular embodiments, the porous material 1002 has a thickness of about 150 µm to about 200 µm. The porous material 1002 can be, for example, filter paper or chromatographic paper. The porous material 1002 can be of any dimension. In some embodiments, the porous material 1002 is a strip, having a length several times its width, as depicted in FIGS. 10A and 10B. For example, the porous material 1002 may be a strip having a length of 40 mm and a width of 5 mm.

In some embodiments, the porous material is cellulose filter paper, ashless filter paper, nitrocellulose filter paper, a glass microfiber filter, porous polyethylene sheets, polyvinylidene difluoride (PVDF) paper, or chromatography paper. Other porous materials are also considered such as flat materials coated with a layer of absorbent material such as silica gel, cellulose powder, or alumina oxide. In certain embodiments, the porous material is a general-purpose cellulose filter paper, a qualitative cellulose filter paper, a quantitative ashless cellulose filter paper, a quantitative hardened ashless cellulose filter paper, or a wet strengthened filter paper. Examples of general purpose cellulose filter papers include, but are not limited to Grade 0858, Grade 0903, Grade 201 qualitative, Grade 202 qualitative, Grade 226 qualitative, Grade 2589 A, and Grade 520 a filter papers.

Examples of qualitative cellulose filter papers include, but are not limited to Grade 1, Grade 2, Grade 3, Grade 4, Grade 5, Grade 6, Grade 588, Grade 591, Grade 595, Grade 597, Grade 597 L, Grade 598, Grade 602 h, and Grade 602EH qualitative filter papers. Examples of quantitative hardened ashless cellulose filter papers include, but are not limited to Grade 589/3, Grade 40, Grade 41, Grade 42, Grade 43, and Grade 44 quantitative ashless filter papers. Examples of quantitative hardened ashless cellulose filter papers include, but are not limited to Grade 540, Grade 541, and Grade 542 hardened ashless cellulose filter papers. Examples of wet strengthened cellulose filter papers include, but are not limited to Grade 113, Grade 114, Grade 1573, Grade 1575, Grade 91, and Grade 93 qualitative wet strengthened filter papers. Examples of chromatographic paper includes, but are not limited to Grade 1 Chr, Grade 17 Chr, Grade 2 Chr, Grade 20 Chr, Grade 2668 Chr, Grade 2727 Chr, Grade 3 Chr, Grade 31ET Chr, Grade 3MM, Grade 4 Chr, and Grade 54 SFC cellulose chromatography papers. In certain embodiments, the porous material is Grade 31ET Chr cellulose chromatography paper. In other embodiments, the porous material is Grade 3MM Chr cellulose chromatography paper. The filter papers provided as examples above are Whatman filters, available from GE Healthcare Lifesciences, although filter papers from other manufacturers having similar properties to those listed above are also considered.

Those of skill in the art will be able to select an appropriate porous material for use in the SPE strips and related methods described herein. Parameters that influence a filter's effectiveness and appropriateness for a particular use include, but are not limited to pore size and particulate retention, adsorption, pH, surface properties, thickness, and wet strength. Those of skill in the art will be able to select a porous material appropriate for use with a particular sample (e.g., a biological sample such as blood).

SPE strips 1000 of the present disclosure include an SPE element 1004. In certain embodiments, the SPE element 1004 is formed on the porous membrane 1002. The SPE element 1004 can be formed on the porous membrane 1002, for example, by spotting or otherwise applying a slurry of SPE powder onto the porous membrane 1002 and allowing the slurry to dry. The SPE powder can be any powder (i.e., sorbent) useful as the solid phase in SPE. The SPE powder can be, for example, a reverse phase sorbent material, including but not limited to C8 sorbent, C12 sorbent, C18 sorbent, Strata-X sorbent, and Strata-XL sorbent. Specialized sorbents falling under these various types of sorbents, as well as other sorbents, are also contemplated. In other embodiments, SPE element 1004 is pre-formed and secured to porous membrane 1002. SPE element 1004 can be secured to porous membrane 1002 by, for example, an adhesive. Preferably, the adhesive is inert and will not interfere with extraction or the analysis by mass spectrometry.

On-strip or on-cartridge sample preparation presents certain challenges not encountered in traditional solid phase extraction procedures. Typically, reverse-phase SPE materials are not water-wettable, thus requiring pressure to force an aqueous biofluid through the SPE sorbent. A small amount of organic solvent may also be added to the aqueous test sample to promote passage of the sample through the solid phase. Neither of these solutions is feasible with the SPE strips or cartridges disclosed herein.

Another challenge is that typical SPE columns must be conditioned with solvents and water prior to adding the sample, and the column cannot be allowed to dry out before the sample is applied. A few SPE sorbents, such as polymeric SPE sorbents are water-wettable, and have reverse phase-type retaining character, such as those available from Sigma-Aldrich®, Agilent Technologies®, Phenomenex®, and Waters®. These materials are also not affected by drying out prior to sample application like traditional silica SPE materials.

In certain embodiments, the SPE element 1004 does not require a conditioning/equilibration step. The SPE powder can be selected based on its binding affinity for the analytes of interest (e.g., new psychoactive substances (NPS)). In some embodiments, SPE element 1004 includes a polymeric, water-wettable, reverse phase-type SPE powder. With the benefit of this disclosure, those of skill in the art will be able to select an appropriate SPE powder for use in the SPE strips, autosampler cartridges, and related methods described herein.

In some embodiments, SPE powder is mixed with a binder and formed into a slurry for spotting or otherwise applying to the porous membrane 1002. The binder can be any substance that can act as an adhesive to help bind together the SPE powder. In some embodiments, the binder is corn starch. The binder can be mixed with the SPE powder at a concentration range of: about 0.5% by mass to about 10% by mass; about 1% by mass to about 5% by mass; or at a concentration of about 3% by mass.

A slurry of SPE powder or SPE powder and binder can be formed by combining the SPE powder or SPE powder and binder with water. In some embodiments, the water is heated (e.g., boiling). A slurry can be prepared by adding water in a ratio (volume:mass) of about 0.5:1, about 1:1, about 2:1, about 3:1, or about 4:1 to SPE powder or SPE and binder.

The amount of slurry to be applied to the porous material 1002 will depend on the width of the porous material 1002 and the biofluid to be sampled. In certain embodiments, sufficient slurry is applied to the porous material to cover an approximately square section, with the square having the width of the porous material, and a thickness of about 0.1 to 1 mm when dry. The thickness of the SPE element 1004 can be selected based on the properties of the biofluid to be sampled. For example, a thinner SPE element may be used with an oral fluid sample, and a thicker SPE element with a urine or plasma sample. In certain embodiments, for example, 10 µl of slurry is applied to a 5 mm-wide strip of porous material 1002 for extraction from oral fluid, and 20 µl of slurry is applied to a 5 mm-wide strip of porous material 1002 for extraction from urine or plasma.

Optionally, an SPE strip includes a reinforcing element 1006. When included, reinforcing element 1006 is placed atop the slurry once it has been applied to the porous material 1002. As the slurry dries and forms SPE element 1004, the reinforcing element provides another surface for the slurry to adhere to and increases the ruggedness of the device once the slurry has dried. In some embodiments, the reinforcing element 1006 has approximately the same dimensions as a surface of the SPE element. For example, if the top surface of the SPE element is 5 mm×5 mm, the reinforcing element to be placed atop the SPE element is about 5 mm×5 mm. In certain embodiments, the reinforcing element 1006 comprises a porous material similar to that of porous material 1002. The reinforcing element 1006 can be the same material as porous material 1002, or a different material. In certain embodiments, reinforcing element 1006 is filter paper or chromatographic paper, as described above for porous material 1002.

It is to be understood that SPE element 1004 as depicted in FIG. 10A is not applied to porous material 1002 in a dried, rigid form, but rather as a slurry as described above, and that FIG. 10A is merely an exploded view illustrating the various elements of SPE strip 1000 as depicted in FIG. 10B.

FIG. 10B depicts an embodiment of an SPE strip 1000 incorporating a reinforcing element 1006.

FIG. 10C depicts another embodiment of an SPE strip. SPE strip 2000 of FIG. 10C is similar to SPE strip 1000 of FIGS. 10A and 10B, but includes an additional support layer 2008, and has a differing geometry. SPE strip 2000 includes a porous material 2002, an SPE element 2004, optional reinforcing element 2006, and support layer 2008. Porous material 2002, SPE element 2004, and optional reinforcing element 2006 corresponds to porous material 1002, SPE element 1004, and optional reinforcing element 1006 of SPE strip 1000 of FIGS. 10A and 10B, which are described above. As illustrated, SPE strip 2000 includes two sections of porous material, with a first section having a width that is greater than the second section. The second section extends outwardly from the first section, and provides a substrate for the SPE, which is disposed on the second section. In some embodiments, the second section is approximately square. The SPE element can have a width approximately the equal to the width of the second section.

Support layer 2008 is provided to give SPE strip 2000 additional mechanical strength and to prevent biofluid from saturating a spray tip when inserted into a sampler cartridge. In some embodiments, support layer 2008 is omitted (i.e., it is optional). In some embodiments, the SPE strip 1000 includes a support layer similar to support layer 2008 of SPE strip 2000. The support layer can be a plastic sheet, such as, for example, Derlin or acetal, although other materials providing sufficient mechanical support and liquid separation from the spray tip are also contemplated.

In certain embodiments, it may be advantageous to have a larger porous material 2002, as depicted in FIG. 10C, particularly when larger sample volumes are to be used. For example, whereas the SPE strip 100 may be a 5×40 mm strip, the first section of porous material of SPE strip 200 may be 15×35 mm strip.

The SPE strip 2000 includes a smaller section at one of its ends or sides. The smaller section may be, for example, square or rectangular. SPE powder/SPE powder with binder slurry is applied to this smaller section of SPE strip 2000 to form SPE element 2004 thereon. Extraction is thus localized, occurring at this smaller section, or extraction component 2010.

Methods are provided for collecting and concentrating analytes from a biological sample. In some embodiments, such methods include contacting an SPE element, or a reinforcing element overlying an SPE element, of an SPE strip described herein with a biological sample. In certain embodiments, the biological sample is one of plasma, urine, and saliva. The SPE element or reinforcing element overlying the SPE element can be contacted with the biological sample by applying a volume of the biological sample to the SPE element or reinforcing element overlying the SPE element. This can be accomplished by, for example, a pipette or other measured volumetric device. The volume of biological sample applied to the SPE element or reinforcing element overlying the SPE element can be, for example, between about 25 µl and 200 µl. The volume of biological sample to be applied can vary by sample type, and by solid phase sorbent used. For example, the volume of saliva to be spotted or otherwise applied can be about 50 µl, while the volume of plasma or urine can be about 100 µl. In some embodiments, the SPE strip is allowed to dry, resulting in a dried SPE strip.

In certain embodiments, the biological sample is from an individual having consumed or otherwise ingested, injected, used, smoked, etc. a new psychoactive substance (NPS) such as, for example, fentanyl, synthetic cannabinoids, synthetic psychedelic tryptamines, and psychedelic phenethylamines.

The SPE strips described herein offer an inexpensive and powerful means for improving NPS paper spray detection limits. As established by the Examples, the SPE strips effectively concentrate certain analytes for paper spray mass spectroscopy. By passing the biological sample through the SPE element, analytes of interest are retained and concentrated within the SPE element. As described herein, the SPE element having retained analytes therein can then be used as the sample source in a paper spray mass spectrometry method.

In certain embodiments, the method for collecting and concentrating analytes from a biological sample results in the collection and concentration of fentanyl, a synthetic cannabinoid (e.g., AB-CHMINACA), a synthetic psychedelic tryptamine, a psychedelic phenethylamine, a metabolite of these, or any combination thereof.

In another aspect, provided herein are methods for analyzing one or more analytes in a biological sample. As illustrated in FIGS. 11A and 11B, in some embodiments, such methods include: securing an SPE element described herein to a paper spray tip, wherein the SPE element includes a biological sample; positioning the SPE element that includes the biological sample and the paper spray tip in functional proximity with a mass spectrometer; applying a volume of a solvent to the SPE element that includes the biological sample to cause one or more analytes from the SPE element to pass from the SPE element to the paper spray tip; applying electrical potential to the paper spray tip to ionize at least a portion of the one or more analytes; and analyzing the ionized portion of the one or more analytes by mass spectrometry. In certain embodiments, the SPE element including the biological sample is subjected to a clean-up step prior to application of the solvent, wherein a volume of, for example, highly purified water is applied to the SPE element including the biological sample. The volume of highly purified water used in the clean-up step can be approximately the same as the volume of sample originally applied to the SPE element.

In some embodiments, the methods for analyzing one or more analytes in a biological sample further involve including a stable isotopic label (SIL) for each analyte to be target. The SIL is added to the SPE element having the biological sample or to the paper tip before the solvent is applied to the sample substrate having the biological sample.

In certain embodiments, the SPE element with biological sample is secured to the paper spray tip by a clip or other fastener, or a paper spray mass spectrometry cartridge. The clip can be, for example, an alligator clip (see FIG. 11A). In some embodiments, the clip can function to both secure the SPE element with sample to the spray tip and to apply a voltage to the spray tip.

Mass spectrometers useful in the methods described herein are known in the art. The mass spectrometry systems are not particularly limited and can be any system that ionizes a chemical analyte and subsequently analyzes and sorts the ions based on the mass to charge ration. Mass spectrometry systems useful in the methods described herein include, but are not limited to the Thermo Fisher Scientific Q-Exactive Focus orbitrap mass spectrometer, the Thermo® TSQ® Vantage (Thermo Finnigan), and the Sciex® Qtrap 5500 (Sciex). The SPE element including the biological sample and the paper spray tip are positioned in functional proximity with the mass spectrometer. That is, they are placed in a sufficient configuration to allow for the mass spectrometer to take up analyte ions generated during application of the electrical potential.

In certain embodiments, the solvent is selected to elute one or more chemical analytes from the SPE element and any underlying portion of the porous material to the paper spray tip. In an embodiment, the solvent is 9:1 acetonitrile:water with 100 ppm formic acid, although other solvents are also contemplated. The volume of solvent is sufficient to elute the one or more chemical analytes from the SPE element to the paper spray tip.

An electrical potential sufficient to ionize at least some of the one or more analytes (i.e., a portion thereof) is applied to the paper spray tip. Methods for paper spray ionization are known in the art. In some embodiments, about 3.0 to about 5.5 kV are applied to the paper spray tip for a predetermined period of time. In certain embodiments, the electrical potential is applied to the paper spray tip for about 1-2 minutes, such as, for example, about 100 seconds.

Following ionization, the mass spectrometer conducts an analysis on the ionized portion of the one or more analytes and detects the identity and concentration of analytes present. In certain embodiments, the mass spectrometer detects the presence and concentration of one or more NPSs' or metabolites thereof. In particular embodiments, the mass spectrometer detects the presence and concentration of at least one of fentanyl and AB-CHMINACA.

In certain embodiments, the methods of analyzing one or more analytes in a biological sample provided herein are automated. The SPE element including biological sample of the present disclosure can be incorporated into cartridges compatible with paper spray mass spectrometry systems capable of rapidly screening multiple samples.

In one aspect, provided herein are paper spray mass spectrometry cartridges for use with a paper spray mass spectrometry system capable of rapidly screening multiple samples. In some embodiments, the paper spray mass spectrometry cartridge is configured to secure an SPE element described herein having a biological sample deposited thereon to or against a paper spray tip. The SPE element is secured to or against the paper spray tip so that when a solvent is applied to the SPE element including the biological sample, one or more chemical analytes retained by the SPE element pass from the SPE element to the paper spray tip. In certain embodiments, the paper spray mass spectrometry cartridge includes a housing and at least one conductive element. The housing can include a base and a top, the top configured to snap into or around the base to form a cartridge assembly, causing the SPE element described herein having a biological sample deposited thereon to be secured to or against the paper spray tip. The housing top further includes an opening to allow application of a solvent to the SPE element having the biological sample deposited thereon. In certain embodiments, the cartridge assembly includes at least one conductive element In certain embodiments, and as depicted in FIGS. 13A-13C, the paper spray mass spectrometry cartridge is configured to accept the SPE element-end of an SPE strip. The SPE element end of the strip is inserted, the top of the housing is snapped into or around the base, causing the SPE element having the biological sample to be secured to or against the paper spray tip (FIG. 13B). The SPE strip is then forcibly withdrawn from the cartridge, leaving the SPE element retained within the cartridge (FIG. 13C).

Once the SPE element having the biological sample is retained in the spectrometry cartridge and secured against the paper spray tip, a solvent is applied to the SPE element including the biological sample, and paper spray mass spectrometry is carried out. In some embodiments, a plurality of such cartridges can be used in a high throughput paper spray mass spectrometry system.

FIG. 12 depicts another embodiment of a mass spectrometry cartridge housing top, wherein the SPE element is disposed in a rear solvent well of a paper spray mass spectrometry cartridge. While mass spectrometry cartridges having an SPE column have been described for use in paper spray mass spectrometry, it was surprisingly found that the simpler SPE element formed in the rear solvent well of a paper spray mass spectrometry cartridge effectively concentrated analytes of interest from whole blood, improving detection limits relative to spotting whole blood directly on the spray paper. FIG. 12A depicts the mass spectrometry cartridge housing top alongside a waste pad. The waste pad is sufficiently absorbent to retain excess whole blood as it is applied to and passes through the SPE element. In some embodiments, the waste pad aids in wicking, or drawing, the whole blood sample through the SPE element. In some embodiments, the SPE element disposed in the rear solvent well of paper spray mass spectrometry cartridges of 3A is formed directly in the paper spray mass spectrometry cartridge. For example, the rear solvent well can be temporarily sealed, and a volume of SPE powder slurry is deposited therein and allowed to dry before the temporary seal is removed, leaving behind the SPE element firmly adhered to the cartridge. The SPE powder can be any powder (i.e., sorbent) useful as the solid phase in SPE. The SPE powder can be, for example, a reverse phase sorbent material, including but not limited to C8 sorbent, C12 sorbent, C18 sorbent, Strata-X sorbent, and Strata-XL sorbent. Specialized sorbents falling under these various types of sorbents, as well as other sorbents, are also contemplated. A few SPE sorbents, such as polymeric SPE sorbents are water-wettable, and have reverse phase-type retaining character, such as those available from Sigma-Aldrich®, Agilent Technologies®, Phenomenex®, and Waters®. These materials are also not affected by drying out prior to sample application like traditional silica SPE materials. The SPE powder can be selected based on its binding affinity for the analytes of interest (e.g., new psychoactive substances (NPS)). With the benefit of this disclosure, those of skill in the art will be able to select an appropriate SPE powder for use in the autosampler cartridges.

In some embodiments, SPE powder is mixed with a binder and formed into a slurry for applying to the solvent well of the paper spray mass spectrometry cartridge. The binder can be any substance that can act as an adhesive to help bind together the SPE powder. In some embodiments, the binder is corn starch. The binder can be mixed with the SPE powder at a concentration range of: about 0.5% by mass to about 10% by mass; about 1% by mass to about 5% by mass; or at a concentration of about 3% by mass. A slurry of SPE powder or SPE powder and binder can be formed by combining the SPE powder or SPE powder and binder with water. In some embodiments, the water is heated (e.g., boiling). A slurry can be prepared by adding water in a ratio (volume:mass) of about 0.5:1, about 1:1, about 2:1, about 3:1, or about 4:1 to SPE powder or SPE and binder.

The amount of slurry to be applied to the solvent well of the paper spray mass spectrometry cartridge will depend on the width and depth of the solvent well and the biofluid to be sampled. In certain embodiments, sufficient slurry is applied to the solvent well to completely block an outlet of the solvent well. The thickness of the SPE element formed in the solvent well can be selected based on the properties of the biofluid to be sampled. In certain embodiments, for example, 10 μl of slurry is applied to the solvent well for extraction from whole blood.

Methods for collecting and concentrating analytes from a biological sample using the paper spray mass spectrometry cartridge having an SPE element are provided. Such embodiments include contacting the SPE element of the cartridge with a biological sample, such as whole blood, although other biological samples such as plasma, urine, and saliva may also be collected using the described SPE element cartridges. The SPE element can be contacted with the biological sample by depositing a volume of the biological sample into the solvent well of the cartridge, as depicted in FIG. 12B. In some embodiments, a waste pad is positioned under the solvent well to absorb, and in certain instances wick, the biological sample (see FIGS. 12A-12C). The volume of biological sample deposited in the solvent well can be deposited as one or more aliquots, and should be sufficient to allow for the sample (or each aliquot thereof) to pass through the SPE element, although flow through the SPE element may be promoted by use of a waste pad having a wicking property. In some embodiments where the biological sample is whole blood, 70 μl of whole blood, provided as two 35 μl aliquots, is deposited in the solvent well of the cartridge. While this volume is provided as an example, in some embodiments a biological sample of from about 15 μl to several hundred microliters can be used. In some embodiments, the SPE element cartridge is allowed to dry following application of the biological sample (see FIG. 12C). In some embodiments, the SPE element, either before or after a drying step, is washed using highly purified water. The washed SPE element cartridge can then either be dried or immediately analyzed by paper spray mass spectrometry.

In certain embodiments, the biological sample applied to the SPE element of the cartridge is from an individual having consumed or otherwise ingested, injected, used, smoked, etc. a new psychoactive substance (NPS) such as, for example, fentanyl, synthetic cannabinoids, synthetic psychedelic tryptamines, and psychedelic phenethylamines.

The SPE cartridges described herein offer an inexpensive, simple, and powerful means for improving NPS paper spray detection limits. As established by the Examples, the SPE element cartridges effectively concentrate analytes for paper spray mass spectroscopy. By passing the biological sample through the SPE element disposed within the solvent well of the cartridge, analytes of interest are retained and concentrated within the SPE element. As described herein, the SPE element of the cartridge having retained analytes therein can then be used as the sample source in a paper spray mass spectrometry method. The SPE element cartridges described herein can be used for collecting and concentrating analytes from a biological sample including fentanyl, a synthetic cannabinoid (e.g., AB-CHMINACA), a synthetic psychedelic tryptamine, a psychedelic phenethylamine, a metabolite of these, or any combination thereof.

Following collection and concentration of analytes in the SPE element of a cartridge described herein, the cartridge housing top bearing the SPE element with biological sample and/or analytes therefrom is snapped into or around a base to form a cartridge assembly (see FIG. 12D). The cartridge assembly further includes at least one conductive element and a paper spray tip.

The cartridge assembly having the SPE element with biological sample and/or analytes can then be subjected to paper spray mass spectrometry, wherein a solvent is applied to the SPE element, causing the analytes retained in the SPE element to transfer to the paper spray tip. In some embodiment, multiple cartridge assemblies can be used in a high throughput paper spray mass spectrometry system.

EXPERIMENTAL EXAMPLES

Experimental Example 1—Preservation of Cannabinoids by Sesame Oil

Figure 4:
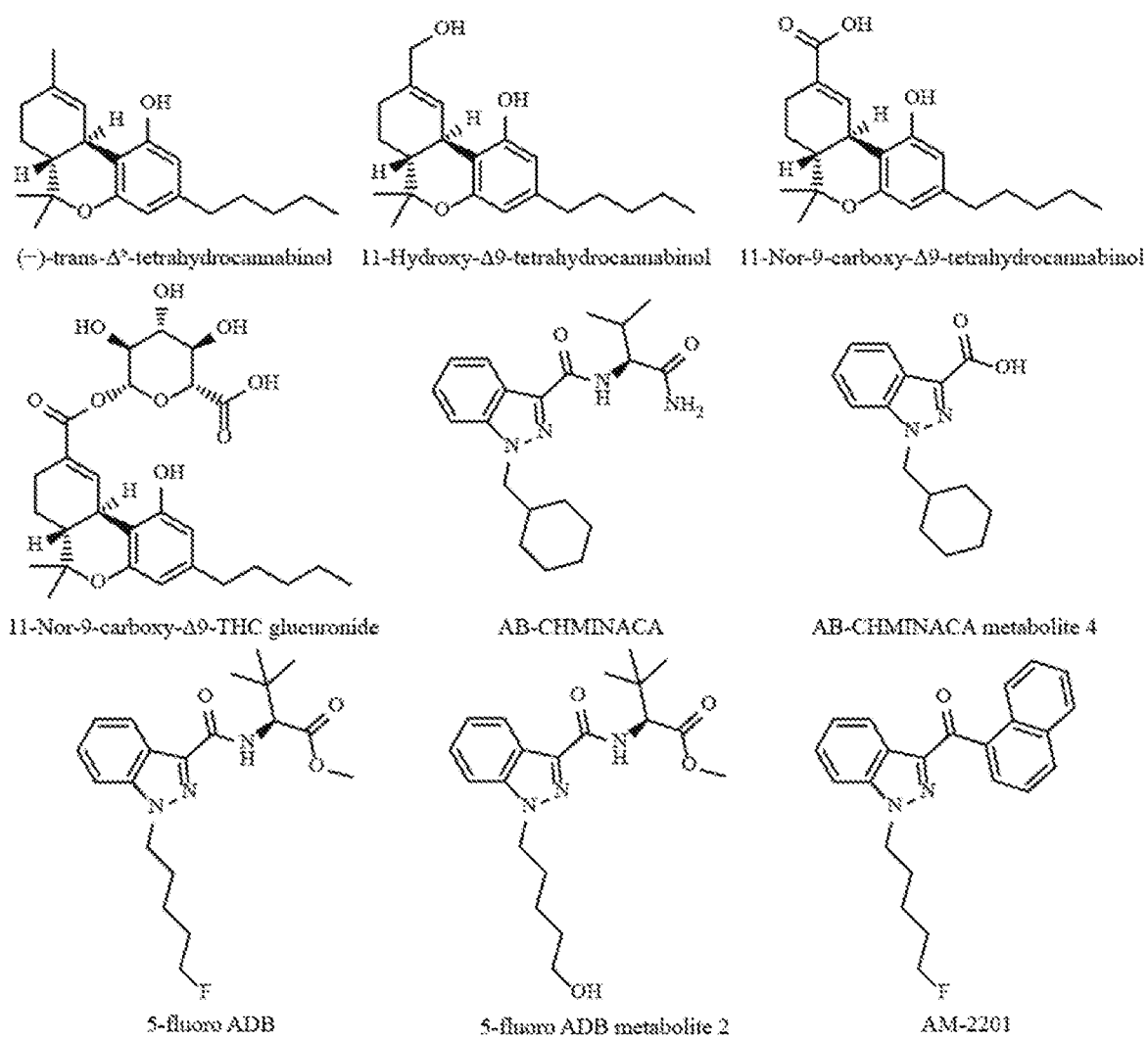
FIG. 4 illustrates select cannabinoid chemical structures.

In one example, the ability of sesame oil to preserve different cannabinoids overnight was evaluated relative to oleic acid, a major component of sesame seed oil, and mineral oil. Fentanyl was included as a non-cannabinoid analyte comparison. Urine samples were spiked at 1 µg/mL for (−)-trans-$\Delta^9$-tetrahydrocannabinol (THC), 11-Hydroxy-$\Delta^9$-tetrahydrocannabinol (11-OH-THC), 11-Nor-9-carboxy-$\Delta^9$-tetrahydrocannabinol (THC-COOH), 11-Nor-9-carboxy-$\Delta^9$-THC glucuronide (THC glucuronide), AB-CHMINACA, AM-2201 and fentanyl in a glass vial. The structures for the cannabinoids are depicted in FIG. 4.

The urine samples were spotted in 5 µL aliquots using a glass capillary onto 5 mm×5 mm squares of 31ET chromatography paper, with or without 5 µL of the different oils absorbed to the chromatography paper, and allowed to dry for 1 hour or 1 day at room temperature on the counter. After drying, the sample squares were spotted with 2.5 µL of methanol containing 500 ng/mL of the stable isotopic labels (SILs) THC D3, THC-COOH D3, AB-CHMINACA D4, AM-2201 D5 and fentanyl D5 in methanol. THC glucuronide and 11-OH-THC used THC D3 for an internal standard.

Figure 5:
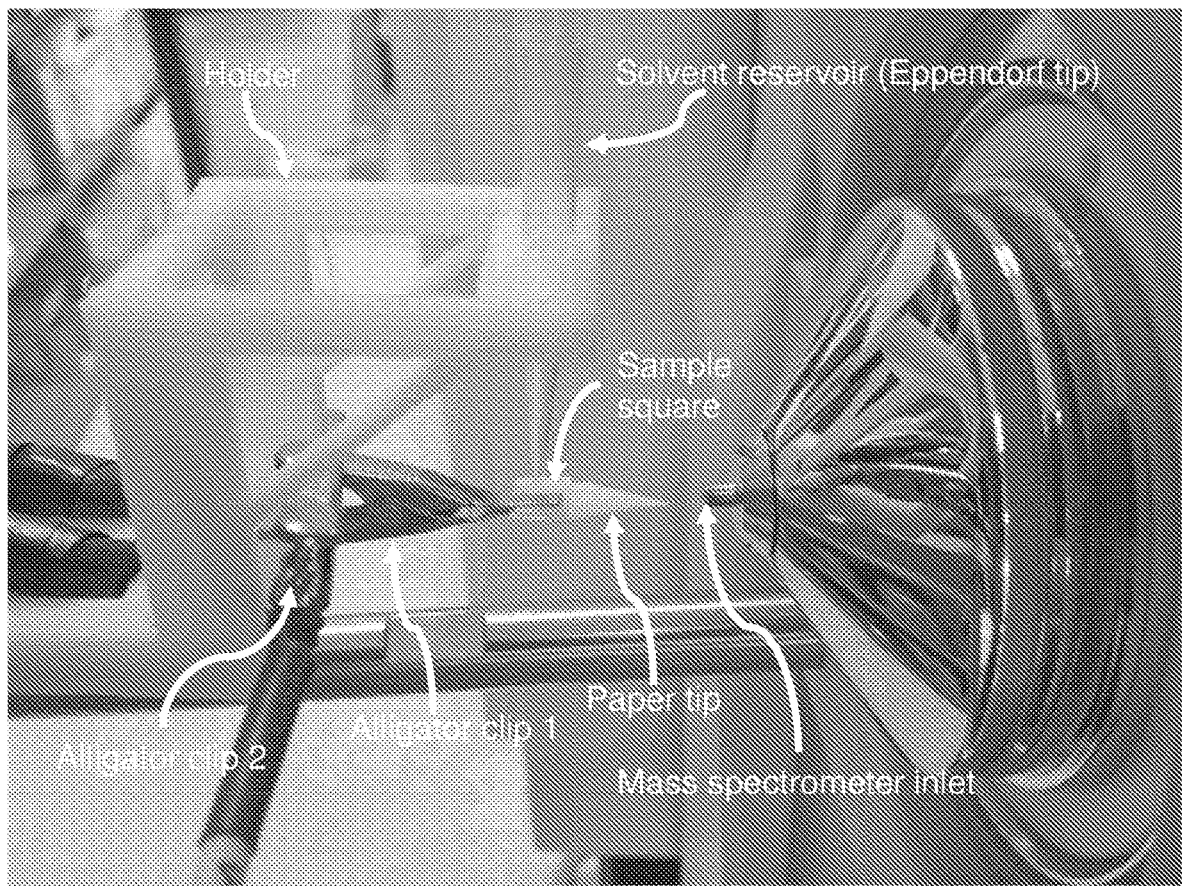
FIG. 5 is a photograph of a paper spray set-up according to an embodiment.

Analysis was carried out using a holder that minimized contact between plastic, the mass spectrometry sample substrate, and the paper spray tip (see FIG. 5). The holder supports an Eppendorf tip that holds solvent and an alligator clip that holds the sample square and paper tip. The paper tip was positioned in front of the inlet of a Thermo Fisher Scientific Q-Exactive Focus orbitrap mass spectrometer and 60 µL of solvent (80:20 acetonitrile:methanol with 25 mM sulfuric acid), was added to the Eppendorf tip. After the solvent flowed through the sample square to the paper spray tip clipped beneath it, 4.5 kV of voltage was applied via a secondary alligator clip for 1 minute. The instrument was run in parallel reaction monitoring (PRM) mode and the area under the curve for the most abundant fragment for each compound was integrated. The ratios of the area under the curve for the analyte divided by its SIL were calculated and compared between samples dried for different lengths of time and with different oils.

(−)-trans-$\Delta^9$-tetrahydrocannabinol (THC) and its metabolites can be difficult to analyze because they are unstable. Additionally, due to their hydrophobicity, a significant portion of THC can be lost from aqueous matrices like urine to plastic containers. To its ability to preserve THC in urine spots, sesame seed oil was added to the paper used to store the sample. Two additional oils were also tested as a comparison to determine whether sesame seed oil is specifically required, or if the major component of sesame seed oil, oleic acid, or a non-fatty acid oil (mineral oil), would also preserve THC. The amount of analyte remaining was measured as a relative amount compared to the SIL spotted shortly before analysis. Preservation was measured by determining the percent decrease between samples that were dried for an hour and samples that were dried for a day. Results are summarized and presented in Table 1.

TABLE 1

Percent change in analyte signal (relative to freshly spotted internal standard) for dried urine samples after 24 hours storage versus one hour.

| Analyte | No Preservative | Sesame Oil | Oleic Acid | Mineral Oil |
|---|---|---|---|---|
| THC | −92% | −7% | −100% | −95% |
| 11-OH-THC | −89% | −32% | −100% | −71% |
| THC-COOH | −88% | −6% | −96% | −53% |
| AB-CHMINACA | −16% | −12% | −41% | −19% |
| AM-2201 | −29% | −16% | −23% | −42% |
| Fentanyl | −34% | 7% | −25% | −29% |

Without sesame oil, THC and its metabolites showed a significant drop over the course of a day while the two synthetic cannabinoids and fentanyl did not, indicating that the synthetic drugs were more stable than the natural cannabinoids in the dried urine spot. Of the three oils tested, only sesame seed oil effectively preserved THC. Sesame seed oil is a mixture of fatty acids, antioxidants and other natural products.

Long term preservation was evaluated by finding the detection limits of analytes after 1, 7, and 27 days of storage at room temperature in the dark. A calibration curve was generated in urine spiked at 0.5, 5, 10, 100, 500 and 1000 ng/mL for THC, 11-OH-THC, THC-COOH, AB-CHMINACA, AM-2201, and fentanyl. The internal standard was an SIL spiked into each calibrator at 100 ng/ml. Two replicates were extracted and analyzed for each concentration as well as three blanks. Calibration curves with or without sesame oil were analyzed after 1, 7, and 27 days. Samples were stored in the dark at room temperature in a loosely covered plastic dish. The slope and Y-intercept were determined by linear regression with a weighting factor of $1/X^2$. Samples showing no signal or signal lower than three standard deviations above the average blank signal were omitted. Detection limits were calculated as three times the standard error of the Y-intercept divided by the slope.

The preservation effects of sesame seed oil are best illustrated by looking at the calibration curves for THC without sesame seed oil before and after 27 days of storage (FIGS. 6A and 6B, respectively) compared to with sesame seed oil over the same length of time (FIGS. 6C and 6D, respectively).

TABLE 3

Lowest detectable urine concentration (ng/mL) after paper strip extraction with and without sesame seed oil after storage at room temperature.

| Analyte | Day 1 No Oil | Day 1 Oil | Day 7 No Oil | Day 7 Oil | Day 27 No Oil | Day 27 Oil |
|---|---|---|---|---|---|---|
| THC | 2 | 1 | 30 | 1 | ≥500* | 3 |
| 11-OH-THC | 20 | 4 | 30 | 4 | ≥1000* | 4 |
| THC-COOH | 10 | 5 | 130 | 30 | ≥1000* | 120 |
| AM-2201 | 0.8 | 1 | 1 | 0.6 | 4 | 0.8 |
| AB-CHMINACA | 1 | 3 | 1 | 1 | 3 | 2 |
| Fentanyl | 2 | 3 | 0.8 | 3 | 2 | 7 |

*Detection limits significantly above the 100 ng/mL internal standard are rough estimates.

The synthetic cannabinoids showed minimal change over time, with or without the addition of oil (Table 3). THC and 11-OH-THC show a measurable increase in the lowest detectable concentration over time without sesame seed oil.

THC-COOH showed significant degradation over time even with sesame seed oil, albeit still improved over no preservative.

Experimental Example 2—Paper Strip Extraction

In another example, the ability of sesame seed oil to concentrate analytes as the wicked through the oil coated paper was investigated. A subset of analytes was selected to include both natural and synthetic cannabinoids as well as other pharmaceuticals with varying physical properties. After the sample was flowed through the oil spot, the paper strip was cut into pieces and analyzed for drug distribution throughout the strip.

Strips of 3MM chromatography paper were cut into 5 mm×40 mm strips, and 2.5 µL of sesame seed oil was spotted at one end of each strip. Urine was spiked at 100 ng/mL for atenolol, alprazolam, carbamazepine, diazepam, gabapentin, fentanyl, AB-CHMINACA, AM-2201, THC glucuronide and THC. Paper strip extraction was carried out by applying 50 µL aliquots of the urine samples to the end of the strip containing the sesame oil and allowed to dry. After drying, the strips were then cut into 5 mm increments (see FIGS. 7A and 7B), and each segment was spiked with 5 µL of a 500 ng/mL solution of the SILs: THC D3, THC-COOH D3, AB-CHMINACA D4, AM-2201 D5, and fentanyl D5 in methanol.

The individual squares were analyzed by paper spray mass spectroscopy and the ratio between the analyte and the SIL was plotted as a function of distance traveled through the paper strip. Three strips were analyzed with and without sesame seed oil and the results were averaged. To get a more comprehensive view of the behavior of analytes during paper strip extraction, the list of analytes included: THC and the more hydrophilic metabolite THC-glucuronide, two synthetic cannabinoids (AB-CHMINACA and AM-2201), fentanyl, and a selection of other pharmaceuticals (alprazolam, atenolol, carbamazepine and diazepam). If the ratio for the analyte to internal standard was constant for each increment, then the analyte did not preconcentrate, whereas if the ratio decreased rapidly from the first 5 mm segment, then the analyte preconcentrated. Data for four different drugs demonstrating the different behaviors are depicted in FIG. 8.

The cannabinoids (THC, THC glucuronide, and both synthetic cannabinoids) decreased significantly by the third segment (10-15 mm) regardless of the presence of sesame seed oil on the paper. All the other analytes except for diazepam had a more uniform distribution throughout the paper strip regardless of the presence of oil. Diazepam showed an even distribution without oil but was more concentrated in the first 10 mm with oil. The distribution of the drugs was not strictly determined by hydrophobicity. While all the molecules that concentrated at the head of the strip are hydrophobic, the fact that the more hydrophilic THC glucuronide also concentrated suggests additional interactions played a role.

Experimental Example 3—Preconcentration Effects on Detection Limits

In another example, the effects of preconcentration by paper strip extraction on paper spray mass spectrometry detection limits were examined.

That THC still had a low ng/ml detection limit with paper strip extraction but without sesame seed oil after 24 hours (Table 3), while 90% of THC directly spotted on paper was gone in the same amount of time (Table 1) suggested that preconcentration could significantly improve detection limits. Samples were prepared in oral fluid and urine by either using paper strip extraction (preconcentrating) or direct spotting on paper for a total of four combinations to determine whether this method made a noticeable impact on detection limits. Urine was spiked at 0.5, 5, 25, 100, 500 and 1000 ng/mL of THC, 11-OH-THC, THC-COOH, AB-CHMINACA, AM-2201, 5F-ADB and AB-CHMINACA metabolite 4 and 100 ng/mL SIL for each analyte except 11-OH-THC and THC-COOH, which used the SIL for THC. Paper strip extraction was carried out as described above and direct spotting was done by spotting 5 µL directly onto 5 mm segments of paper. For samples prepared with oil but without paper strip extraction, a strip of paper with oil was prepared as normal, after the oil distributed on the paper the first 5 mm segment was removed and spiked with urine. Two replicates at each concentration and three blanks were analyzed after 1 and 28 days to evaluate the effects of preconcentration and preservation.

To test the effects of preconcentration on detection limits and preservation, biofluids were stored on paper with sesame seed oil with and without preconcentration and analyzed after 1 day and 28 days (Table 4). Oral fluid was added as a second non-invasive biofluid (Table 5).

TABLE 4

Lowest detectable urine concentration (ng/mL) with and without paper strip extraction after storage at room temperature with sesame seed oil.

| | Day 1 | | Day 28 | |
| --- | --- | --- | --- | --- |
| Urine | Without Concentration | With Concentration | Without Concentration | With Concentration |
| THC | 20 | 2 | 10 | 2 |
| 11-OH-THC | 9 | 4 | 70 | 20 |
| THC-COOH | 200 | 10 | ≥500* | 40 |
| AM-2201 | 0.2 | 0.2 | 0.2 | 0.2 |
| AB-CHMINACA | 1 | 0.2 | 1 | 2 |
| AB-CHMINACA M4 | 130 | 60 | 70 | 80 |
| 5F-ADB | 2 | 0.3 | 0.3 | 0.3 |

*Detection limits well above the 100 ng/mL internal standard are rough estimates.

TABLE 5

Lowest detectable oral fluid concentration (ng/mL) with and without paper strip extraction after storage at room temperature with sesame seed oil.

| | Day 1 | | Day 28 | |
| --- | --- | --- | --- | --- |
| Oral Fluid | Without Concentration | With Concentration | Without Concentration | With Concentration |
| THC | 20 | 1 | 30 | 1 |
| 11-OH-THC | 4 | 3 | 70 | 5 |
| THC-COOH | 10 | 3 | ≥1000* | 60 |
| AM-2201 | 0.06 | 0.08 | 0.2 | 0.08 |
| AB-CHMINACA | 4 | 0.6 | 3 | 2 |
| AB-CHMINACA M4 | 50 | 100 | 100 | 100 |
| 5F-ADB | 2 | 0.2 | 2 | 0.2 |

*Detection limits well above the 100 ng/mL internal standard are rough estimates.

Tables 4 and 5 indicate a noticeable improvement to detection limits resulting from preconcentration for THC. THC-COOH behaved as in Table 3; showing heightened detection limits after 28 days, even with oil. However, for both THC-COOH and 11-0H-THC without preconcentration, there was an increase in detection limits after 28 days for both biofluids. This suggests that there is a secondary mechanism for the elimination of the two THC metabolites that isn't abated by preconcentration or sesame seed oil. The metabolite AB-CHMINACA M4, which is more hydrophilic than AB-CHMINACA, showed worse detection limits than AB-CHMINACA under all conditions. The fact that the three metabolites studied show worse results than the original analytes suggest that paper strip extraction with sesame seed oil is less effective for metabolites. This could be due to metabolites typically being less hydrophobic than the original analyte. However, the detection limits for THC without preconcentration ranged from 10-30 ng/mL while with preconcentration the limit ranges between 1-2 ng/mL; showing that preconcentration does lower detection limits, for certain analytes. AM-2201 and AB-CHMINACA had consistent results regardless of the biofluid, preconcentration, or storage time. 5F-ADB in most cases showed about an order of magnitude improvement in its detection limit when performing paper strip extraction. These results indicate that paper strip extraction improves the detection limits for synthetic cannabinoids relative to directly spotting the analyte on paper, but that this effect is analyte dependent. More importantly, the detection limits for the synthetic cannabinoids did not get worse with the addition of oil, meaning that both natural and synthetic cannabinoids can be detected with the same method.

Experimental Example 4—Automated Analysis

In another example, it was evaluated whether the paper strip extraction could be used for rapid screening.

The main attractions of paper spray mass spectrometry are its ease of use and short analysis times. Any modifications to the technique should maintain the speed and simplicity of the technique; otherwise those modifications defeat the purpose of paper spray. Ideally, the analysis would also compatible with automation to enable high throughput analysis. A disposable cartridge was designed to be analyzed using a commercially available autosampler to demonstrate the potential for simple, fast, and automated implementation of paper strip extraction. The cartridge included two parts that snapped together around the sample square and paper spray tip. The top half of the cartridge was 3D printed in polypropylene (top part of FIG. 9A) and the bottom half came from an injection molded paper spray autosampler cartridge (bottom part of FIG. 9A). Polypropylene was selected for the top half due to its resistance to organic solvents. When the top half was snapped onto the bottom half, it made a seal around the sample square such that solvent flowed through the sample to the paper spray substrate. As depicted, the top half incorporated a steel ball bearing, used as an electrical contact.

A calibration curve was generated using the prepared cartridges to determine; the LOD calculated from the calibration curves are shown in Table 6. THC-COOH was also run in this experiment, but there were insufficient data points for a calibration curve. This was unexpected because THC analysis performed similarly to previous experiments. The three synthetic cannabinoids and two metabolites likewise behaved similarly. It's possible that some interferent eluting from the 3D printed plastic specifically affected THC-COOH ionization. Beyond this anomaly the autosampler cartridge results showed that the paper strip extraction technique is compatible with automation.

TABLE 6

Detection limits in ng/mL in oral fluid using sesame seed oil and paper strip extraction in a half 3D printed autosampler cartridge.

| Analyte | LOD |
| --- | --- |
| THC | 4 |
| 5F-ADB | 0.1 |
| 5F-ADB M2 | 0.5 |
| AB-CHMINACA | 6 |
| AM-2201 | 0.1 |
| AB-CHMINACA M4 | 20 |

Paper strip extraction was evaluated here as a means of analyzing natural and synthetic cannabinoids. As the detection limits for synthetic cannabinoids were not significantly worse when comparing paper strip extraction to direct spotting (see Tables 4 and 5), nor were they significantly worse after extended storage (see Tables 3-5), the usefulness of paper strip extraction lies in having a technique capable of simultaneous and rapid detection of both synthetic and natural cannabinoids. Paper spray coupled to paper strip extraction represents a new opportunity to rapidly screen for both synthetic and natural cannabinoids from urine or oral fluid samples.

Experimental Example 5—Making SPE Extraction Strips and Cartridges

In one example, solid phase extraction (SPE) strips and cartridges were prepared. A slurry of SPE powder and a binder was coated onto the end of a strip of chromatography paper and allowed to harden into a porous solid. The slurry was prepared by adding boiling water in a 2:1 ratio (volume:mass) to SPE powder containing cornstarch at 3% by mass. The slurry was heated by submerging a container with the slurry therein in a boiling water bath for 5 minutes. The slurry was spotted in 10 μL aliquots for oral fluid experiments and 20 μL aliquots for urine or plasma on the end of wet strips of 31ET chromatography paper. The strips were 5×40 mm for oral fluid experiments (see FIGS. 10A and 10B) and 15×35 mm with a 5×5 mm square segment at one end for urine and plasma (see FIG. 10B). Adding a 5×5 mm square of grade 4 filter paper to the top of the slurry on the strip added another surface for the slurry to adhere to and increased ruggedness of the device once the slurry dried (see FIGS. 10A-10C). For whole blood extraction, the top half of an autosampler cartridge was removed and the rear solvent well was sealed on the bottom with aluminum foil (see FIGS. 13 and 14A). The well was filled with 10 μL of slurry and allowed to dry before removing the foil. After drying, the mixture of starch and SPE powder was rugged enough to be handled without fracturing. The finished extraction devices for oral fluid, urine or plasma, and whole blood are shown in FIGS. 10A-10C, 13, and 14A.

Experimental Example 6—Analyte Retention

In another example, the SPE extraction strips of Example 5 were tested to determine their ability to concentrate certain analytes. Biofluids (i.e., plasma, oral fluid, and urine were spiked at 500 ng/mL of the prescription drugs atenolol, carbamazepine, fentanyl and diazepam and the NPSs carfentanil, AB-CHMINACA and AM-2201, as well as the metabolite norfentanyl. Extraction was carried out by flowing 50 μL of the biofluid through the SPE region at the end of each strip. Following extraction and drying, the strip was cut into 5 mm increments and spiked with 5 μL of 500 ng/mL stable isotope labeled (SIL) analogs of the analytes except for norfentanyl and carfentanil, which used fentanyl-d5.

Paper spray MS was carried out by using an alligator clip to attach the sample square onto a paper tip and positioning it in front of the inlet of a Thermo Fisher Scientific Q-Exactive Focus orbitrap mass spectrometer. Two 30 µL aliquots of 9:1 acetonitrile:water with 100 ppm formic acid were added to a solvent well consisting of an Eppendorf tip contacting the sample square. After adding the solvent, ionization was carried out by applying 4.5 kV of voltage to the paper for 1.7 minutes. The MS was run in parallel reaction monitoring mode (PRM), measuring the MS/MS spectrum for each analyte and its SIL. Each 5 mm increment was analyzed separately and the area under the curve during each run was calculated for each analyte and its SIL. Drug retention was evaluated by calculating the ratio between the analyte in the square divided by the SIL and normalizing the value to the ratio from the first 5 mm of the strip.

The first test of the SPE extractions strips was to confirm that passing biofluid through the SPE region retained the analytes. To this end, three different biofluids were selected and spiked with fentanyl, carfentanil, and norfentanyl (a fentanyl analogue and metabolite); AB-CHMINACA and AM-2201 (synthetic cannabinoids); as well as the pharmaceuticals diazepam, atenolol, and carbamazepine. Pharmaceuticals were included because physical and chemical properties such as log P and pKa are not known for many NPS; including analytes with known physical properties helps determine whether any observed trends are related to those properties. After extraction and dividing the strip into 5 mm increments, each segment was spiked with an internal standard. The ratio between the analyte and the SIL IS was used to determine if the analytes were concentrated. A similar experiment was carried out with a strip of 3MM chromatography paper without SPE material as a comparison. The 3MM paper was used instead of 31ET because 3MM was found to concentrate certain analytes even without SPE material, and that property needed to be considered when evaluating the effectiveness of the SPE coated strip. The results were normalized to the first 5 mm increment and the results for carbamazepine, fentanyl, and AB-CHMINACA are shown in FIGS. 14A-14C, respectively.

For all three biofluids, most of the analytes showed the same trends as carbamazepine (FIG. 14A) and fentanyl (FIG. 14B); significant analyte retention was observed when the SPE material was present but not for plain paper. This result indicated that the SPE material preconcentrates drugs from larger sample volumes much more effectively than plain paper. AB-CHMINACA (FIG. 14C) and AM-2201 showed a different trend in oral fluid and urine samples. In these two matrices, the synthetic cannabinoids tended to concentrate on chromatography paper even without SPE material. This is most likely due to the synthetic cannabinoids' high hydrophobicity. The concentration effect was still more pronounced with SPE present, however. In plasma samples, the synthetic cannabinoids did not show any concentration effects for plain paper. This is likely because of the high protein content in plasma samples, which would have bound the drugs non-specifically and carried them along the strip.

Experimental Example 7—SPE Strip Extraction of Plasma, Oral Fluid, and Urine

In another example, limits of detection in different biofluids were evaluated by analyzing calibration curves with and without SPE extraction. Calibration curves were prepared in plasma, oral fluid, and urine at 0.1, 1, 10, 25, 100 and 1000 ng/mL each of drug or metabolite, with a 100 ng/mL internal standard consisting of SILs. For each biofluid, two measurements were made at each concentration as well as three blank measurements. Extraction was carried out as described in Experimental Example 6, except that 100 µL was extracted for plasma and urine using the paper strip with a larger width (FIG. 10C). After drying, the same volume of milli-Q water (50 µL for oral fluid, 100 µL for plasma and urine) was flowed through the SPE region as a clean-up step. Direct spotting was conducted by spotting 5 µL of biofluid directly on a 5×5 mm square of 31ET. After extraction and drying, the first 5 mm segment containing the SPE material was cut from the rest of the strip and attached to a wedge of 31ET chromatography paper with a point using an alligator clip, and the same was done with the directly spotted squares. Paper spray-MS was carried out as described in Experimental Example 6, except that the spray solvent volume was increased for the SPE samples to two aliquots of 40 µL of solvent. Ratios between the analyte and SIL were determined for each calibration level, and a calibration curve was constructed. Any data points which were lower than three times the standard deviation of the blanks were excluded. Slopes and Y-intercepts were calculated using linear regression with a weighting factor of $1/X^2$. Limits of detection were set at three times the standard error in the Y-intercept divided by the slope.

SPE extraction can lead to lower detection limits if there isn't also an increase in matrix effects. Plasma, oral fluid, and urine were extracted using the SPE paper strip and washed with milli-Q water to minimize matrix effects caused by water soluble components like salts. Limits of detection from the SPE strip and from directly spotting the biofluids were calculated based on their calibration curves (Table 7).

Of the 27 drug-matrix combinations, 14 demonstrated an improvement in detectable limit by a factor of ten or more for SPE strip extraction relative to direct paper spray MS. For oral fluid samples, significant improvement in detection limits was obtained for carfentanil, diazepam and norfentanyl. Plasma and urine samples showed large improvements in detection limits for 11 of the drug-matrix combinations, ranging from around a factor 10 for acetyl fentanyl in urine and diazepam in plasma to upwards of 50 for atenolol in plasma.

TABLE 7

Lowest detectable concentration (ng/mL) in plasma, urine, and oral fluid when extracted using SPE strip and when directly spotting the biofluid on paper (no SPE). Oral fluid SPE strip extraction was carried out with half the amount of SPE and half the amount of biofluid volume as plasma or urine.

| | Plasma | | Urine | | Oral Fluid | |
| --- | --- | --- | --- | --- | --- | --- |
| | SPE | No SPE | SPE | No SPE | SPE | No SPE |
| AB-CHMINACA | 0.2 | 5 | 2 | 5 | 0.4 | 0.5 |
| Acetyl Fentanyl | 0.1 | 2 | 0.01 | 0.1 | 0.01 | 0.02 |
| AM-2201 | 2 | 3 | 0.3 | 0.9 | 0.6 | 0.07 |
| Atenolol | 0.2 | 10 | 1 | 4 | 0.5 | 2 |
| carbamazepine | 0.2 | 3 | 0.2 | 2 | 0.04 | 0.04 |
| carfentanil | 0.02 | 0.5 | 0.01 | 0.4 | 0.04 | 0.4 |
| Diazepam | 0.2 | 2 | 2 | 2 | 0.03 | 0.4 |
| Fentanyl | 0.2 | 1 | 0.02 | 0.2 | 0.03 | 0.03 |
| Norfentanyl | 0.4 | 3 | 4 | 80 | 0.03 | 0.4 |

Sample volume is an important consideration during method development. For plasma and urine, 100 μL was found to give better detection limits than by extracting only 50 μL of biofluid. There is a limit to the volume of biofluid that can be extracted by this method, however. The rate of flow through the SPE material slows at higher volumes because the wicking rate decreases as the sample wicking distance increases. It is also possible that components of the biofluid clog the SPE material, which would have a cumulative effect at higher volumes. Also, a lower sample volume was necessary for oral fluid because the enzymes in oral fluid degraded the starch binder; the SPE material was no longer held together and had to be analyzed with care not to spill the powder. To improve robustness of oral fluid analysis by this method, a water wettable binder that is not degraded by enzymes found in oral fluid can be used. Despite the lower extraction volume, oral fluid still showed marked improvements in detection limits for three of the nine analytes.

Experimental Example 8—SPE Cartridge Extraction of Whole Blood

In another example, the effectiveness of the cartridges of Experimental Example 5 to concentrate certain analytes from whole blood was examined. A calibration curve was prepared as described in Experimental Example 7, but in whole blood using an autosampler cartridge with SPE material in the solvent slot, as described in Experimental Example 5 (FIGS. 13 and 14A). Two aliquots of 35 μL of whole blood were flowed through the SPE to a waste pad consisting of three 1×1 cm squares of grade 1660 cytosep paper (FIG. 12B).

Two aliquots of 75 μL of milli-Q water was applied to the SPE, where it flowed through the SPE material to 31ET chromatography paper waste pads. Cartridges were washed either while the blood was still wet or after two hours of drying at room temperature (FIG. 12C). For direct spotting, 10 μL of blood was spotted directly on the paper inside the autosampler cartridge. The cartridges were then assembled (FIG. 12D) and analyzed as described in Experimental Example 6, except the solvent was 1:1 acetonitrile:methanol with 100 ppm formic acid. Direct whole blood analysis was carried out with 60 μL of spray solvent, whereas SPE whole blood samples used 80 μL. Calibration curves and limits of detection were calculated as described in Experimental Example 7.

SPE extraction of biofluids like plasma has been shown to be an effective way to improve limits of detection. Analyzing whole blood would be faster as it would eliminate the added step of removing red blood cells. However, whole blood is viscous and therefore difficult to flow appreciable quantities through SPE material. Furthermore, whole blood does not flow laterally easily because it tends to clog as it travels through normal chromatography paper. Both of these factor makes it incompatible with SPE strip extraction. To overcome these problems, the apparatus depicted in FIGS. 13 and 14A was devised. Here, whole blood was flowed vertically through the SPE solid contained within the solvent well of a paper spray autosampler cartridge. The blood sample flowed through SPE material onto a waste pad of three layers of cytosep lateral blood fractionation paper (FIG. 12A). This fractionation paper is designed to wick whole blood and to separate out plasma from the slower eluting red blood cells in the process. The dry SPE-starch solid was found to firmly adhere to the acetal plastic cartridge throughout the extraction process without adhesives. After applying blood sample, the SPE material was washed with milli-Q water either when the whole blood was dry or while the blood was still wet. Washing removed most of the coloration of the SPE material (FIG. 11D) and the limits of detection were compared to direct spotting of the whole blood as shown in Table 8.

TABLE 8

Limits of detection (ng/mL) for analytes in whole blood when directly spotted on paper (no SPE), extracted using SPE then washed while dry, and extracted using SPE then washed while still wet.

| | No SPE | Dry wash | Wet Wash |
|---|---|---|---|
| AB-CHMINACA | 1 | 0.3 | 0.2 |
| Acetyl Fentanyl | 0.08 | 0.01 | 0.01 |
| AM-2201 | 2 | 0.3 | 0.2 |
| Atenolol | 3 | 0.4 | 0.3 |
| Carbamazepine | 2 | 0.03 | 0.2 |
| Carfentanil | 0.5 | 0.1 | 0.09 |
| Diazepam | 20 | 0.3 | 0.3 |
| Fentanyl | 0.3 | 0.03 | 0.2 |
| Norfentanyl | 0.7 | 0.7 | 0.4 |

Extraction of whole blood demonstrated a consistent improvement of detection limits for most analytes. The washing procedure didn't depend on whether the blood was dry or wet, except in the case of fentanyl and carbamazepine. Washing after the whole blood was dry performed better relative to wet.

The methods of Experimental Examples 6, 7, and 8 demonstrate the ability of paper spray with integrated SPE to improve detection limits for synthetic cannabinoids, opioids, and pharmaceuticals in a variety of matrices. To be useful, the detection limits must be close to biologically relevant concentrations. For synthetic cannabinoids in general this is difficult as there are many potential targets and the potency of each is often unknown. In 2014, two studies on AB-CHMINACA exposure found ranges of 0.4-14.3 ng/mL in plasma of patients experiencing acute delirium and seizures and whole blood concentrations of 0.6-10 ng/mL in suspected impaired drivers. In another study looking at synthetic cannabinoids similar to AM-2201 in postmortem plasma samples, concentrations were found at 16.3, 140 and 0.86 ng/mL for MAM-2201, AM-1220 and AM-2232 respectively. These studies give a rough idea of the concentration range expected for these specific analytes, which is in the low to sub-ng/mL range. Looking at the results in Tables 7 and 8, the detection limits for the synthetic cannabinoids AB-CHMINACA and AM-2201 were in the low to sub-ng/ mL range for the three biofluids. This is close to the biological concentrations, indicating the suitability of the method as a screening technique.

For fentanyl and fentanyl analogues, the biologically relevant concentration range depends on the potency. Acetylfentanyl, for example, has been found at over 100 ng/mL in blood samples from several intoxications and fatalities, while carfentanil has been found in the 0.01-0.617 ng/mL ranges. From the results in Table 8, the method is adequate for detection of acetylfentanyl with detection limits at 0.01 ng/mL, but may fail to detect carfentanil in cases of intoxication where whole blood concentrations are below 0.1 ng/ml. If the matrix were plasma or urine, however, the detection limit would be significantly lower.

Beyond the two illicit drug classes of synthetic cannabinoids and fentanyl analogues, a number of pharmaceuticals were also evaluated. They included the beta blocker atenolol, the anticonvulsant carbamazepine and the benzodiazepine diazepam and were included as examples of non-illicit targets with documented physical properties. The fact that the three pharmaceuticals showed measurable improvements to their detection limits in various biofluids suggests a universal improvement for hydrophobic drugs using these methods. This could be useful for therapeutic drug monitoring of more potent drugs where chromatographic techniques are too time consuming and expensive.

Experimental Example 9—Cartridge for Implementation of SPE Strip Extraction

In another example, a cartridge with a built-in SPE strip extraction assembly was produced. The top half of a commercially available autosampler cartridge was removed and replaced with a 3D printed top section, as depicted on the left of FIG. 13A. The top section was designed to flow biofluid and solvent through the SPE region of an extraction strip. The top section was modeled in Sketchup and printed using polypropylene filament on an Ultimaker 2 extended+ 3D printer. The SPE extraction strip was adhered to a 0.35 mm thick piece of Delrin plastic, as depicted on the right side of FIG. 13A, and positioned on top of a paper spray tip within the cartridge in FIG. 13B. The SPE extraction strip was perforated with a razor blade between the SPE region and the waste strip. The bottom half of the cartridge, shown in the middle of FIG. 13A, had plastic cut away from one side with a razor blade to make room for the extraction strip. After extraction, the excess paper was removed along with the Delrin as shown in FIG. 13C.

The cartridges were developed to offer an SPE method that can easily be integrated with paper spray-MS. Of the two means of doing this, SPE strip extraction of plasma, urine and oral fluid are the simpler option for ease of use. Due to the viscosity of whole blood multiple waste pads are required for extraction and washing, making it a more complicated method to implement with paper spray-MS than the SPE strip. SPE strip extraction can be added to a commercially available autosampler cartridge with a few modifications as illustrated in FIGS. 13A-13C. First, the top half of the autosampler cartridge can be replaced with an alternative version that can snap onto the original bottom half of the cartridge and fits around the SPE region (element) of the strip when assembled (FIG. 13B) to channel biofluid and solvent. The strip is adhered to a thin strip of Delrin plastic (FIG. 13A) to prevent biofluid from saturating the spray tip beneath during extraction. After extraction, washing, and drying, the waste portion of the strip can be torn along perforation leaving behind the SPE region sitting on top of the spray tip ready for analysis (FIG. 13C). This design is simple, requiring minimal effort to conduct an SPE extraction prior to analysis. This design would work best for plasma or urine extraction as oral fluid has been shown to degrade the starch binder.

While the disclosed subject matter is amenable to various modifications and alternative forms, specific embodiments are described herein in detail. The intention, however, is not to limit the disclosure to the particular embodiments described. On the contrary, the disclosure is intended to cover all modifications, equivalents, and alternatives falling within the scope of the disclosure as defined by the appended claims.

Similarly, although illustrative methods may be described herein, the description of the methods should not be interpreted as implying any requirement of, or particular order among or between, the various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step).

What is claimed is:

1. A solid phase extraction (SPE) strip comprising a porous material and an SPE element disposed thereon,
    wherein the porous material is selected from cellulose filter paper, ashless filter paper, nitrocellulose filter paper, a glass microfiber filter, porous polyethylene sheets, polyvinylidene difluoride (PVDF) paper, chromatography paper, or flat materials coated with an absorbent layer made from silica gel, cellulose, alumina oxide, or other powders, and
    wherein the SPE element comprises a polymeric, water-wettable, reverse phase-type SPE powder adhered to the porous material.

2. The SPE strip of claim 1, wherein the SPE element comprises the polymeric, water-wettable, reverse phase-type SPE powder and a binder.

3. The SPE strip of claim 2, wherein the binder is present in the SPE element at a concentration of about 0.5% by mass to about 10% by mass.

4. The SPE strip of claim 2, wherein the binder is corn starch.

5. The SPE strip of claim 1, further comprising a reinforcing element disposed atop the SPE element and comprises filter paper or chromatographic paper.

6. The SPE strip of claim 1, wherein the porous material includes a first section and a second section, wherein the first section is wider than the second section, the second section extends outwardly from one edge of the first section, and the SPE element is disposed on the second section.

7. The SPE strip of claim 6, wherein the SPE element has a width approximately equal to a width of the second section.

8. The SPE strip of claim 1, further comprising a support layer positioned at a surface of the porous material opposite to that on which the SPE element is disposed.

9. The SPE strip of claim 8, wherein the support layer is a plastic sheet or film selected from Derlin and acetal.

10. The SPE strip of claim 1, wherein the porous material has a thickness of about 150 μm to about 200 μm.

11. A method of analyzing one or more analytes in a biological sample, the method comprising:
    a. securing the SPE element of the SPE strip of claim 1 to a paper spray tip, wherein the SPE element comprises the biological sample and/or analytes from the biological sample;
    b. positioning the SPE element comprising the biological sample and/or analytes from the biological sample and the paper spray tip in functional proximity with a mass spectrometer;
    c. applying a volume of a solvent to the SPE element comprising the biological sample and/or analytes from the biological sample to cause one or more analytes from the biological sample to pass from the SPE element to the paper spray tip;
    d. applying an electrical potential to the paper spray tip to ionize at least a portion of the one or more analytes; and
    e. analyzing the ionized portion of the one or more analytes by mass spectrometry.

12. The method of claim 11, wherein the SPE element is secured to the paper spray tip by a clip or a paper spray mass spectrometry cartridge.

13. The method of claim 11, wherein the biological sample is selected from urine, saliva, and plasma.

14. The method of claim 11, wherein the one or more analytes is selected from: fentanyl, a fentanyl metabolite, a synthetic cannabinoid, a synthetic cannabinoid metabolite, a synthetic psychedelic tryptamine, a synthetic psychedelic tryptamine metabolite, a psychedelic phenethylamine, and a psychedelic phenethylamine metabolite.

15. A paper spray mass spectrometry cartridge comprising a solvent well and a solid phase extraction (SPE) element disposed within the solvent well, wherein the SPE element comprises a polymeric, water-wettable, reverse phase-type SPE powder and a binder.

16. The paper spray mass spectrometry cartridge of claim 15, wherein the binder is corn starch.

17. The paper spray mass spectrometry cartridge of claim 15, wherein the binder is present in the SPE element at a concentration of about 0.5% by mass to about 10% by mass.

\* \* \* \* \*